(12) United States Patent
Ardell et al.

(10) Patent No.: US 11,642,530 B2
(45) Date of Patent: May 9, 2023

(54) NEURAL MODULATION OF AUTONOMIC NERVOUS SYSTEM TO ALTER MEMORY AND PLASTICITY OF THE AUTONOMIC NETWORK

(71) Applicant: THE REGENTS OF THE UNIVERSITY OF CALIFORNIA, Oakland, CA (US)

(72) Inventors: Jeffrey Laurence Ardell, Encino, CA (US); Marmar Vaseghi, Beverly Hills, CA (US); Kalyanam Shivkumar, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 443 days.

(21) Appl. No.: 16/626,101

(22) PCT Filed: Jun. 25, 2018

(86) PCT No.: PCT/US2018/039260
§ 371 (c)(1),
(2) Date: Dec. 23, 2019

(87) PCT Pub. No.: WO2019/005661
PCT Pub. Date: Jan. 3, 2019

(65) Prior Publication Data
US 2020/0206510 A1 Jul. 2, 2020

Related U.S. Application Data

(60) Provisional application No. 62/525,012, filed on Jun. 26, 2017.

(51) Int. Cl.
*A61N 1/36* (2006.01)

(52) U.S. Cl.
CPC ...... *A61N 1/36114* (2013.01); *A61N 1/36062* (2017.08); *A61N 1/36121* (2013.01); *A61N 1/36189* (2013.01)

(58) Field of Classification Search
CPC ............ A61N 1/36114; A61N 1/36062; A61N 1/36121; A61N 1/36189
See application file for complete search history.

(56) References Cited

U.S. PATENT DOCUMENTS

| | | | | |
|---|---|---|---|---|
| 2002/0099418 | A1* | 7/2002 | Naritoku | A61N 1/36064 607/45 |
| 2013/0131746 | A1* | 5/2013 | Simon | A61N 1/3625 607/9 |

* cited by examiner

*Primary Examiner* — Joseph M Dietrich
(74) *Attorney, Agent, or Firm* — Riverside Law LLP

(57) ABSTRACT

The present invention provides systems and methods for modulating the plasticity and/or memory of the autonomic nervous system.

20 Claims, 26 Drawing Sheets
Specification includes a Sequence Listing.

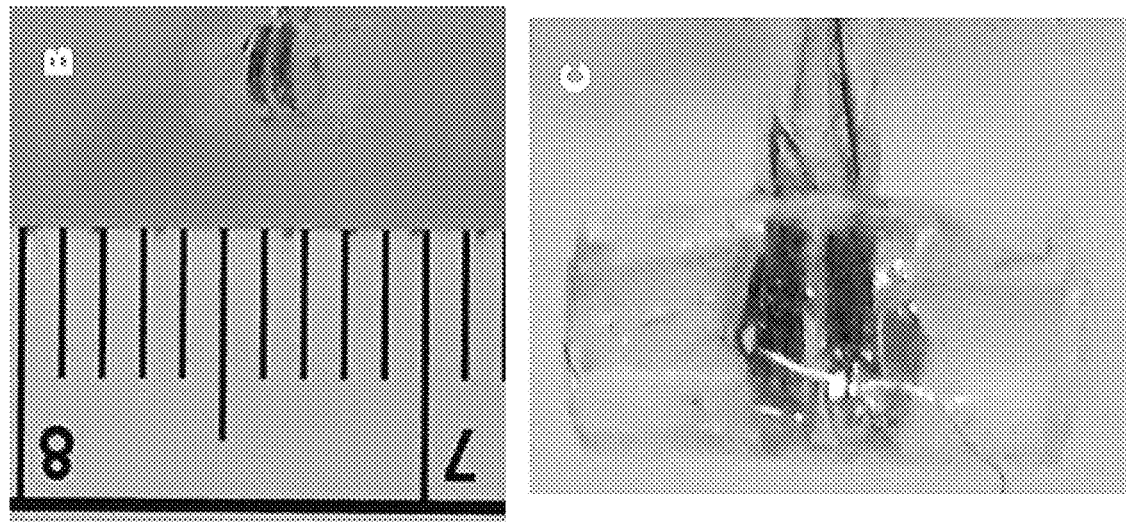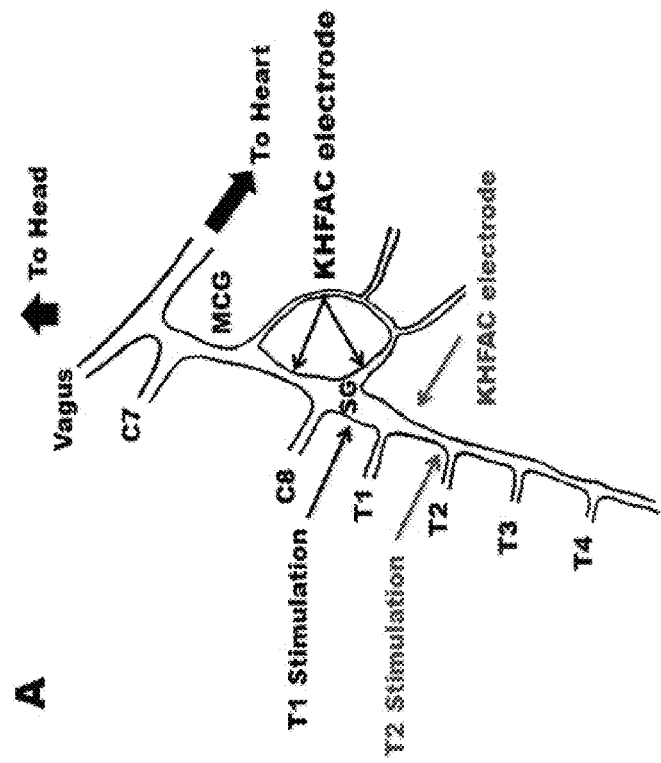
Figure 1A – Figure 1C

| Group | LV +dp/dt mmHg/s | LV -dp/dt mmHg/s | Heart rate beats/mn | LVSP mmHg | BP mmHg |
|---|---|---|---|---|---|
| Control | 2152.3 ± 110.4 | -2542.2 ± 106.5 | 70.3 ± 3.7 | 153.6 ± 4.6 | 127.1 ± 4.8 |
| RW | 1739.9 ± 222.7 | -1920.3 ± 221.4 | 97.1 ± 5.6* | 127.2 ± 10.0 | 112.6 ± 7.9 |
| RW+RCV | 1962.9 ± 225.9 | -2322.7 ± 256.1 | 97.6 ± 8.7* | 140.9 ± 13.6 | 124.4 ± 11.5 |

* $p \leq 0.05$ vs control

Figure 14

| GENE SYMBOL | ACCESSION NUMBER | SEQUENCES | | AMPLICON LENGTH (nt) | TEMP (°C) |
|---|---|---|---|---|---|
| CASP3 | NM_001003042 | TCATTATTCAGGCCTGCCGAGGT ACAAGAAGTCCGCTTCGACTGGT | SEQ ID NO 1 SEQ ID NO 2 | 111 | X |
| HIF1A | NM_001287163 | GTGAACAGAATGGAATGGAGCA GGTCAGTTGTGGTAATCCACTCTC | SEQ ID NO 3 SEQ ID NO 4 | 107 | 65 |
| NR1 | | | | | |
| NR2/GRIN2B | NM_001008719 | CCAATGGCAAGCATGGGAAGAA GAGTGATCCACCGCCATGTA | SEQ ID NO 5 SEQ ID NO 6 | 95 | X used primer "e" |
| GAPDH | AB038240 | TGACACCCACTCTTCCACCTTCGAC CCACCCGGTTGCTTGCTGTAGCCAAATTC | SEQ ID NO 7 SEQ ID NO 8 | 110 | 68 |
| SDHA | XM_535807 | AATCCGTGAAGGCAGAGGCTGTGG GCCGTCTCTGAAATGCCAGGCAGA | SEQ ID NO 9 SEQ ID NO 10 | 111 | 64 |
| b-actin | NM_001195845 | CACTATTGGCAACGAGCGGTTC GTAGTTTCATGATGGCCGAGGA | SEQ ID NO 11 SEQ ID NO 12 | 90 | 68 |
| 18S ribosomal RNA | AY623831 | TCGATGCTCTTAGCTGAGTGTCC GAACCGGGGTCTATTCCATTATTC | SEQ ID NO 13 SEQ ID NO 14 | 125 | 58 | glyceraldehyde-3-phosphate dehydrogenase
succinate dehydrogenase complex, subunit A

Figure 23

| Event | LV+dp/dt mmHg/min | LV−dp/dt mmHg/min | LVDP mmHg | LVSP mmHg | PaBP mmHg | Pw mmHg | Cardiac output l/min | Heart rate beats/min | Stroke volume ml |
|---|---|---|---|---|---|---|---|---|---|
| Baseline 1 | 1532 ± 91 | -1595 ± 77 | 9.5 ± 0.7 | 105.4 ± 3.7 | 14.2 ± 0.8 | 8.8 ± 0.7 | 3.2 ± 0.3 | 98.5 ± 3.0 | 32.7 ± 2.4 |
| LAD CAO | 1459 ± 94 | -1432 ± 72 | 12.6 ± 1.0 * | 98.2 ± 3.2 | 15.8 ± 0.9 * | 10.5 ± 0.9 * | 3.1 ± 0.2 | 108.1 ± 3.9 * | 28.6 ± 1.7 * |
| Reperfusion | 1311 ± 64 * | -1326 ± 63 * | 11.3 ± 1.1 * | 91.1 ± 2.3 * | 15.6 ± 0.9 | 10.3 ± 0.8 * | 2.9 ± 0.3 | 103.2 ± 3.2 | 28.4 ± 2.1 * |
| Baseline 2 | 1379 ± 54 | -1226 ± 48 + | 8.5 ± 0.5 | 84.3 ± 1.3 + | 13.0 ± 0.5 | 7.5 ± 0.4 | 2.3 ± 0.1 + | 91.6 ± 4.7 | 26.7 ± 1.6 + |
| post-MR | 1445 ± 51 | -1110 ± 69 | 14.5 ± 1.1 * | 82.2 ± 2.2 | 15.5 ± 0.7 * | 10.5 ± 0.7 * | 2.4 ± 0.1 | 112.1 ± 3.8 * | 21.5 ± 1.3 * |
| Termination | | | | | | | | | |
| untreated | 1558 ± 137 | -1603 ± 226 | 15.8 ± 3.3 # | 102.2 ± 8.1 | 24.8 ± 3.3 # | 17.3 ± 3.5 # | 2.9 ± 0.2 | 121.5 ± 7.4 # | 24.0 ± 1.9 |
| early SCS | 1530 ± 261 | -1513 ± 208 | 19.0 ± 3.5 # | 101.6 ± 7.8 | 23.5 ± 3.7 # | 18.2 ± 3.1 # | 2.6 ± 0.2 | 122.2 ± 4.1 # | 21.5 ± 1.5 # |
| late SCS | 1330 ± 156 | -1356 ± 136 | 13.8 ± 3.2 | 92.1 ± 7.2 | 25.0 ± 4.1 # | 18.9 ± 5.0 # | 2.2 ± 0.1 # | 113.2 ± 6.1 # | 20.0 ± 1.7 # |

\* p ≤ 0.05 from Baseline 1 or Baseline 2
\+ p ≤ 0.05 Baseline 1 vs Baseline 2
\# p ≤ 0.05 from baseline 1

Figure 24

Table 2

| Blood biomarkers | Baseline | MI - 2 days | MI - 14 days | MR - 2 day | Termination | Reference ranges |
|---|---|---|---|---|---|---|
| Creatine Kinase MB | 2.9 ± 0.5 | 7.1 ± 1.0* | 3.1 ± 0.4† | 2.9 ± 0.3† | 2.3 ± 0.3† | 0.6-6.3 ng/ml |
| Creatine Kinase | 172.0 ± 13.5 | 10366.1 ± 1681.6* | 157.5 ± 12.4 | 822.4 ± 240.1†,# | 357.8 ± 99.1† | 38-234 IU/L |
| Troponin-I | 0.03 ± 0.01 | 30.70 ± 5.96* | 0.18 ± 0.09† | 1.56 ± 0.61* | 0.02 ± 0.01† | 0.00-0.04 ng/ml |

Figure 25

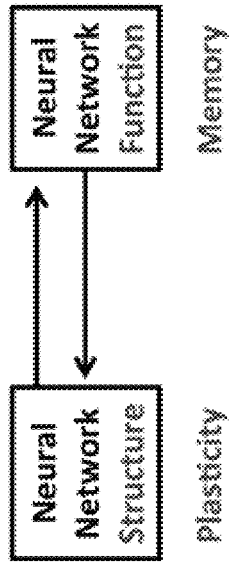

Neural network plasticity — structural adaptation of the cardiac nervous system in response to changing physiological/phathophysiological conditions and/or delivery of energy from an external source

Neural network memory — functional adaptation of the cardiac nerous system due to integration of historical and current information in response to changing physiological/pathophysiological conditions and/or delivery of energy from an external source

Memory and plasticity are interdependent

Figure 26

SEQUENCE LISTING

<160> NUMBER OF SEQ ID NOS: 14

<210> SEQ ID NO 1
<211> LENGTH: 23
<212> TYPE: DNA

```
<213> ORGANISM: Artificial Sequence
<220> FEATURE:
<223> OTHER INFORMATION: chemically synthesized

<400> SEQUENCE: 1
tcattattca ggcctgccga ggt                                          23

<210> SEQ ID NO 2
<211> LENGTH: 23
<212> TYPE: DNA
<213> ORGANISM: Artificial Sequence
<220> FEATURE:
<223> OTHER INFORMATION: chemically synthesized

<400> SEQUENCE: 2
acaagaagtc cgcttcgact ggt                                          23

<210> SEQ ID NO 3
<211> LENGTH: 22
<212> TYPE: DNA
<213> ORGANISM: Artificial Sequence
<220> FEATURE:
<223> OTHER INFORMATION: chemically synthesized

<400> SEQUENCE: 3
gtgaacagaa tggaatggag ca                                           22

<210> SEQ ID NO 4
<211> LENGTH: 24
<212> TYPE: DNA
<213> ORGANISM: Artificial Sequence
<220> FEATURE:
<223> OTHER INFORMATION: chemically synthesized

<400> SEQUENCE: 4
ggtcagttgt ggtaatccac tctc                                         24

<210> SEQ ID NO 5
<211> LENGTH: 22
<212> TYPE: DNA
<213> ORGANISM: Artificial Sequence
<220> FEATURE:
<223> OTHER INFORMATION: chemically synthesized

<400> SEQUENCE: 5
ccaatggcaa gcatgggaag aa                                           22

<210> SEQ ID NO 6
<211> LENGTH: 21
<212> TYPE: DNA
<213> ORGANISM: Artificial Sequence
<220> FEATURE:
<223> OTHER INFORMATION: chemically synthesized

<400> SEQUENCE: 6
gagtgatccc accgccatgt a                                            21

<210> SEQ ID NO 7
<211> LENGTH: 25
<212> TYPE: DNA
<213> ORGANISM: Artificial Sequence
<220> FEATURE:
<223> OTHER INFORMATION: chemically synthesized

<400> SEQUENCE: 7
tgacacccac tcttccacct tcgac                                        25
```

<210> SEQ ID NO 8
<211> LENGTH: 25
<212> TYPE: DNA
<213> ORGANISM: Artificial Sequence
<220> FEATURE:
<223> OTHER INFORMATION: chemically synthesized

<400> SEQUENCE: 8
ccacccggtt gctgtagcca aattc                                    25

<210> SEQ ID NO 9
<211> LENGTH: 24
<212> TYPE: DNA
<213> ORGANISM: Artificial Sequence
<220> FEATURE:
<223> OTHER INFORMATION: chemically synthesized

<400> SEQUENCE: 9
aatccgtgaa ggcagaggct gtgg                                     24

<210> SEQ ID NO 10
<211> LENGTH: 24
<212> TYPE: DNA
<213> ORGANISM: Artificial Sequence
<220> FEATURE:
<223> OTHER INFORMATION: chemically synthesized

<400> SEQUENCE: 10
gccgtctctg aaatgccagg caga                                     24

<210> SEQ ID NO 11
<211> LENGTH: 22
<212> TYPE: DNA
<213> ORGANISM: Artificial Sequence
<220> FEATURE:
<223> OTHER INFORMATION: chemically synthesized

<400> SEQUENCE: 11
cactattggc aacgagcggt tc                                       22

<210> SEQ ID NO 12
<211> LENGTH: 23
<212> TYPE: DNA
<213> ORGANISM: Artificial Sequence
<220> FEATURE:
<223> OTHER INFORMATION: chemically synthesized

<400> SEQUENCE: 12
gtagtttcat ggatgccgca gga                                      23

<210> SEQ ID NO 13
<211> LENGTH: 23
<212> TYPE: DNA
<213> ORGANISM: Artificial Sequence
<220> FEATURE:
<223> OTHER INFORMATION: chemically synthesized

<400> SEQUENCE: 13
tcgatgctct tagctgagtg tcc                                      23

<210> SEQ ID NO 14
<211> LENGTH: 25
<212> TYPE: DNA
<213> ORGANISM: Artificial Sequence
<220> FEATURE:

```
<223> OTHER INFORMATION: chemically synthesized

<400> SEQUENCE: 14
gaaccgcggt cctattccat tattc                                              25
```

NEURAL MODULATION OF AUTONOMIC NERVOUS SYSTEM TO ALTER MEMORY AND PLASTICITY OF THE AUTONOMIC NETWORK

CROSS REFERENCE TO RELATED APPLICATIONS

This application is a U.S. national phase application filed under 35 U.S.C. § 371 claiming benefit to International Patent Application No. PCT/US2018/039260, filed Jun. 25, 2018, which is entitled to priority under 35 U.S.C. § 119(e) to U.S. Provisional Application No. 62/525,012, filed Jun. 26, 2017, each of which is hereby incorporated by reference herein in its entirety.

BACKGROUND OF THE INVENTION

Atrial fibrillation (AF) affects more than three million people a year in the United States, a prevalence that is projected to reach 5.6-12.1 million by 2050 (Go A S et al., 2001, J Am Med Assoc, 285:2370-2375; Naccarelli G V et al., 2009, Am J Cardiol, 104:1534-1539). Despite such prevalence, the underlying mechanisms of AF are not fully understood. Current treatments consist of pharmacological therapies that have been combined with localized atrial catheter-based or surgical ablation (Chen P S et al., 2014, Circ Res, 114:1500-1515; Shen M J et al., 2014, Circ Res, 114:1004-1021). Ablation procedures are associated with complications such as the left atrial stiffness syndrome (Gibson D N et al., 2011, Heart Rhythm, 8:1364-1371), microembolic episodes (Schwarz N et al., 2010, Heart Rhythm, 7:1761-1767), and a risk of symptomatic or silent cerebral ischemia (Gaita F et al., 2010, Circulation, 122: 1667-1673). Such drawbacks have increased the research focus on defining specific neural and cardiac substrate interactions underlying AF and with such information evolving novel nonpharmacological therapeutic options for its management (Zipes D P., 2015, Nat Rev Cardiol, 12:68-69).

Sudden cardiac death (SCD) due to ventricular arrhythmias is the leading cause of mortality in the world, resulting in an estimated four to five million deaths each year (Chugh et al., 2008, *Progress in Cardiovascular Diseases,* 51(3): 213-28). Myocardial infarction (MI) causes changes in the cardiac autonomic nervous system (ANS) that play a crucial role in the genesis of arrhythmias and progression to heart failure (Vaseghi and Shivkumar, 2008, *Prog Cardiovasc Dis,* 50(6):404-19; Shen and Zipes, 2014, *Circulation Research;* 114(6):1004-21). The cardiac neuraxis is responsible for the dynamic regulation of cardiac electrical and mechanical function (Armour, 2004, *Am J Physiol Regul Integr Comp Physiol;* 287(2):R262-71; Ardell and Armour, 2016, Compr Physiol: 1635-1653), and involves neural networks located from the level of the heart (Armour, 2008, *Exp Physiol;* 93(2):165-76; Beaumont et al., 2013, *The Journal of Physiology;* 591(Pt 18):4515-33; Ardell et al, 2016, *J Physiol* 594:3877-3909; Shivkumar et al., 2016, *J. Physiol* 594: 3911-3954) to that of the insular cortex (Oppenheimer and Hopkins, 1994, *Neurocardiology*. New York: Oxford University Press:309-42; Gray et al., 2007, *Proc Natl Acad Sci USA.,* 104(16):6818-23).

Progression of cardiac disease reflects pathological interactions between the cardiac nervous system and the heart (Fukuda et al, 2015, Circ Res 116:2005-2019; Florea et al. 2014, Circ Res 114: 1815-1826). Targeting select elements within this neural network can lead to efficacious results in select cardiac disease states, including atrial arrhythmias, myocardial infarction, and congestive heart failure (Ardell et al, 2016, J Physiol 594:3877-3909; Shivkumar et al., 2016, J Physiol 594: 3911-3954). Advances in bioelectric cardiac therapies are dependent on a clear mechanistic understanding of neural control cardiac function and the impact of bioelectric interventions on the cardiac neural network (Ardell et al, 2017, J Physiol 595: 6887-6903).

Therefore, there is a need for improved bioelectric cardiac therapies that can alter plasticity and memory. The present invention addresses these needs.

SUMMARY OF THE INVENTION

In one aspect, the present invention provides a method for altering the plasticity of a neural structure comprising, delivering energy to an autonomic neural structure (ganglion or nerve), wherein the delivery of energy alters the plasticity of the neural structure during and beyond the delivery. In one embodiment, the effects extend beyond neural structure to which energy is delivered, to the greater autonomic network. In some embodiments, the energy is selected from the group consisting of electrical energy, electromagnetic energy, acoustic energy, and thermal energy.

In one embodiment, one or more electrodes are placed directly in or adjacent to the neural structure by direct surgical access. In one embodiment, one or more electrodes are placed in or adjacent to the neural structure by vascular access. In one embodiment, one or more electrodes are placed in proximity to the neural structure.

In one embodiment, the neural structure is at least one selected from the group consisting of: a nerve or ganglia of the intrinsic cardiac nervous system, a nerve or ganglia of the intrathoracic nerve trunk, a nerve or ganglia of the cervical vagosympathetic nerve trunk, nodose ganglia, petrosal ganglia, a paravertebral sympathetic chain ganglia, the dorsal root ganglia, the spinal cord, and a peripheral distribution of the $9^{th}$, $10^{th}$, or $12^{th}$ cranial nerves.

In one embodiment, the method alters the neural network structure, and wherein the alteration includes one or more changes selected from the group consisting of changes in: neuronal apoptosis potential, neural network interconnectivity, neuronal phenotype, receptors and the neural-myocyte interface.

In one embodiment, the method comprises directly altering the neural structure to which energy is delivered. In one embodiment, the method comprises altering a neural structure that is rostral and/or caudal to the neural structure to which energy is delivered.

In one embodiment, the energy is delivered acutely. In one embodiment, the energy is delivered chronically.

In one aspect, the invention provides a method of altering the function of an autonomic neural structure, comprising delivering energy to an autonomic neural structure (ganglion or nerve), wherein the delivery of energy alters its function during and beyond the delivery. In one embodiment, the effects extend beyond neural structure to which energy is delivered, to the greater autonomic network. In some embodiments, the energy is selected from the group consisting of electrical energy, electromagnetic energy, acoustic energy, and thermal energy.

In one embodiment, one or more electrodes are placed directly in or adjacent to the neural structure by direct surgical access. In one embodiment, one or more electrodes are placed in or adjacent to the neural structure by vascular access. In one embodiment, one or more electrodes are placed in proximity to the neural structure.

In one embodiment, the neural structure is at least one selected from the group consisting of: a nerve or ganglia of the intrinsic cardiac nervous system, a nerve or ganglia of the intrathoracic nerve trunk, a nerve or ganglia of the cervical vagosympathetic nerve trunk, nodose ganglia, petrosal ganglia, a paravertebral sympathetic chain ganglia, the dorsal root ganglia, the spinal cord, and a peripheral distribution of the $9^{th}$, $10^{th}$, or $12^{th}$ cranial nerves.

In one embodiment, the method alters the neural network function, and wherein the alteration includes one or more changes selected from the group consisting of changes in: neural activity, network interconnectivity, and altered neurotransmitter release at the neural-myocyte interface. In one embodiment, neuronal function is altered in a subset or subsets of neurons contained within intrathoracic ganglia including afferents, local circuit, sympathetic or parasympathetic soma. In one embodiment, neuronal function is altered in primary cardiovascular afferent associated with the dorsal root, petrosal or nodose ganglia and their projections to brainstem and spinal cord neural networks.

In one embodiment, the method comprises directly altering the neural structure to which energy is delivered. In one embodiment, the method comprises altering a neural structure that is rostral and/or caudal to the neural structure to which energy is delivered.

In one embodiment, the energy is delivered acutely. In one embodiment, the energy is delivered chronically.

In one embodiment, the delivery of energy is delivered in an open loop by an external control. In one embodiment, the delivery of energy is delivered in a closed-loop.

In one embodiment the energy is delivered upon the detection of a signal. In one embodiment, the signal comprises the identification of neural signature or recordings indicative of adverse autonomic activity and that is recorded from electrodes placed into or on intrathoracic ganglia or intrathoracic axonal projections. In one embodiment, the signal comprises the identification of neural signature or recordings indicative of adverse cardiovascular activity and that is recorded from electrodes placed into or on nodose, petrosal or dorsal root ganglia. In one embodiment, the signal comprises the identification of neural signature or recordings indicative of adverse autonomic activity and that is recorded from electrodes placed into or on the cervical vagosympathetic nerve trunk or paravertebral ganglia. In one embodiment, the signal comprises detection of one or more abnormal chemicals or biomarkers, as detected from one or more sensors within the heart muscle, cardiac chambers or other intravascular sites.

In one aspect, the invention provides a system for modulating the plasticity and/or memory of the autonomic nervous system comprising one or more components for delivering energy to a nerve or ganglion of the autonomic nervous system.

In one embodiment, the system further comprises one or more recording electrodes for measuring the activity of a nerve, ganglia, neuron or electrical activity of the heart. In one embodiment, the systems comprises one for more recording electrodes or sensors for measuring biomarker levels within the heart or vasculature.

In one embodiment, the one or more components comprise one or more stimulating electrodes for applying an electrical stimulus.

In one embodiment, stimulating electrodes are placed dorsal to and utilized in conjunction with one or more components for producing scalable block of efferent projecting axons to the heart. In one embodiment, the one or more components for producing scalable block of efferent projecting axons to the heart are configured for delivering energy for producing the scalable block, wherein the energy is selected from the group consisting of electrical energy, electromagnetic energy, acoustic energy, and thermal energy.

In one embodiment, the evaluation of block efficacy is done manually. In one embodiment, the evaluation of block efficacy is done in close looped fashion and evoked changes in neural signals or cardiac signals are the sensory detect signal against which block efficacy is assessed.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A-FIG. 1C depict the methods of Kilohertz Frequency Alternating Current (KHFAC) stimulation. Bipolar KHFAC electrodes were deployed to region between 1st and 2nd paravertebral ganglia or to the dorsal and/or ventral ansae subclavia (FIG. 1A). Sympathetic efferent projections to the heart were activated at either the 2nd paravertebral (T2) or stellate ganglia (T1) respectively and the blocking efficacy of KHFAC evaluated. These nexus points represent the primary route for afferent projections from heart and sympathetic efferent projections to the heart.

FIG. 5C) were progressively decreased with increases in KHFAC stimulus intensity. Shown are response curves in 7 different animals. 0% reflects no block (full sympathetic response) and 100% reflects complete functional block of sympathetic efferent projections to the heart.

Figures 6A, 6B, 6C:
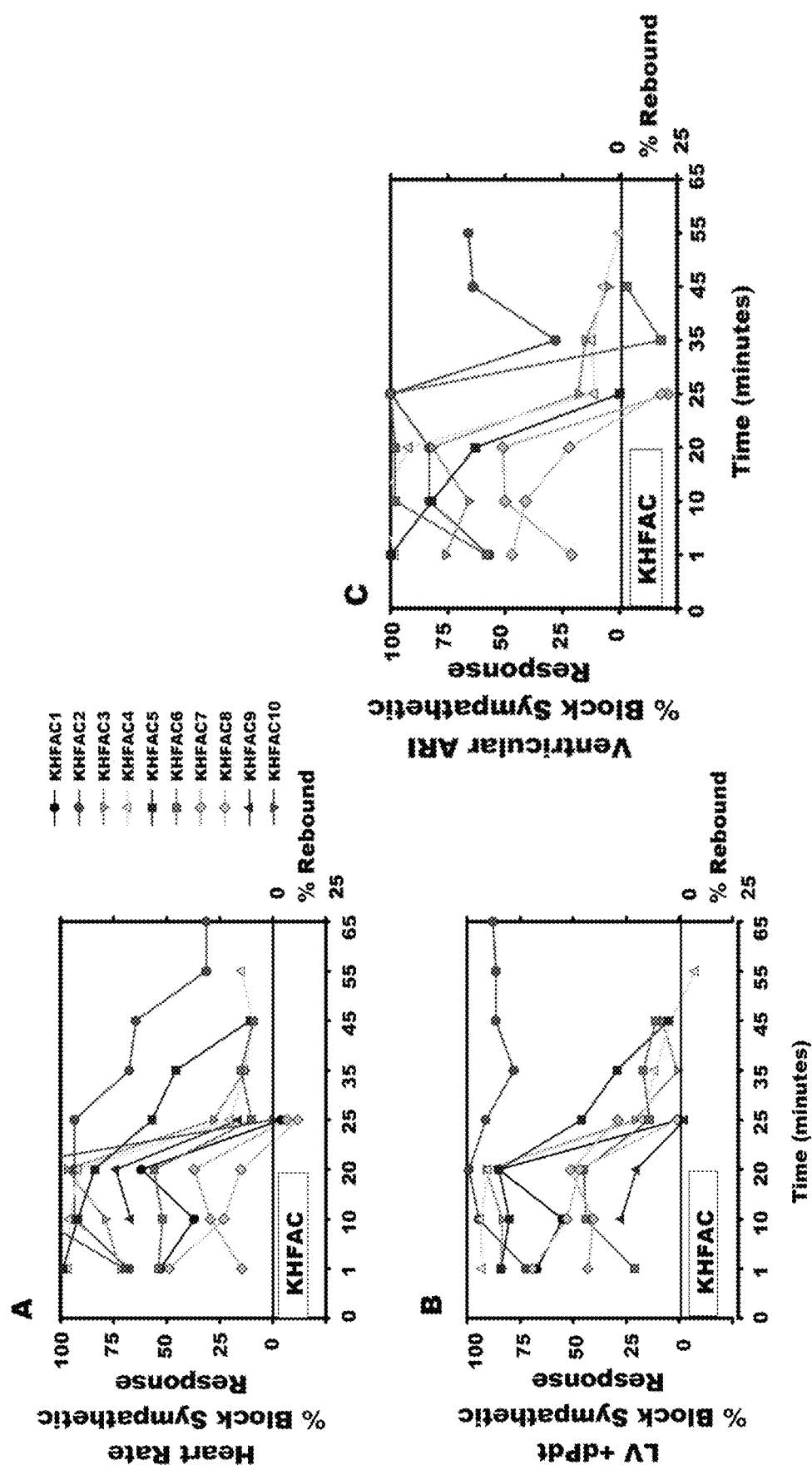

FIG. 6A-FIG. 6C depicts results that KHFAC block demonstrates persistence and memory: Effects of 20 minutes KHFAC on the percentage block of the sympathetic evoked responses during and after KHFAC (n=10 animals). Sympathetic stimulation from right T1 (if KHFAC deployed to ansae) or right T2 (if KHFAC deployed between T1-T2 paravertebral ganglia) was performed at 1 minute, 10 minutes, and 20 minutes of KHFAC. Post KHFAC sympathetic stimulations were performed at 5 minutes and subsequently every 10 minutes for up to 1 hour or until recovery of the response. Shown are the hemodynamic responses for heart rate (FIG. 6A), LV +dP/dt (FIG. 6B) and Ventricular ARI (FIG. 6C). In some cases there was a rebound of the sympathetic response after the 20 minutes of KHFAC with augmented responses (% Rebound). In one animal (KHFAC2) the hemodynamic indices did not recover. In this case, stimulation through the KHFAC electrode (4 hz, 4 ms) demonstrated a normal sympathetic response indicating nerve viability.

Figures 7A, 7B, 7C, 7D:
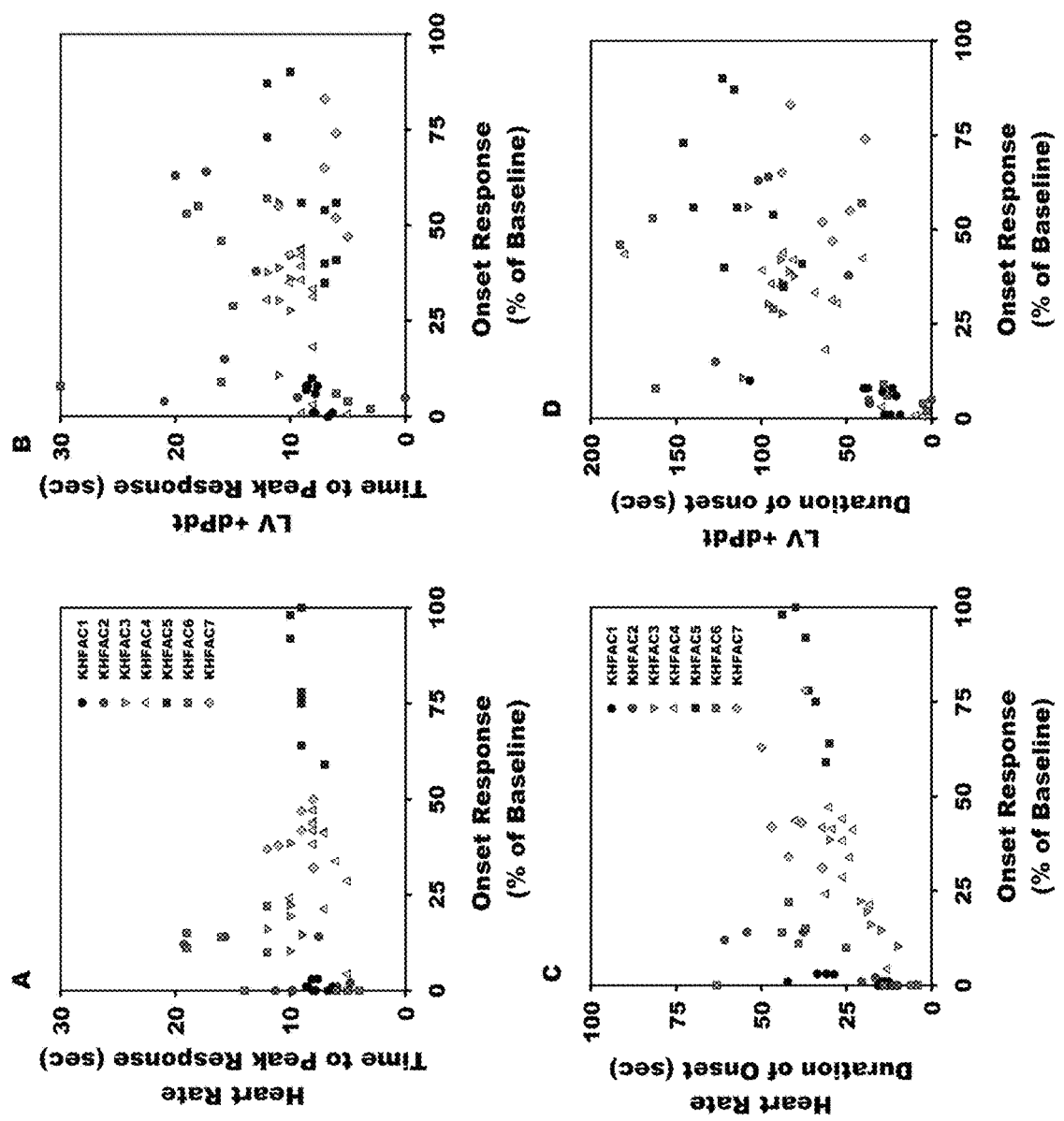

FIG. 7A-FIG. 7D depict the time course of KHFAC onset: FIG. 7A and FIG. 7B shows the time to peak for the various onset responses at initiation of KHFAC. Note that the time to peak onset is relatively constant across the all stimulus protocols (frequency and intensity). FIG. 7C shows the time from start of onset to 66% recovery to baseline for heart rate for all stimulus protocols. Overall, the duration of the onset response is directly related to the magnitude of that response (FIG. 7C and FIG. 7D).

Figure 8:
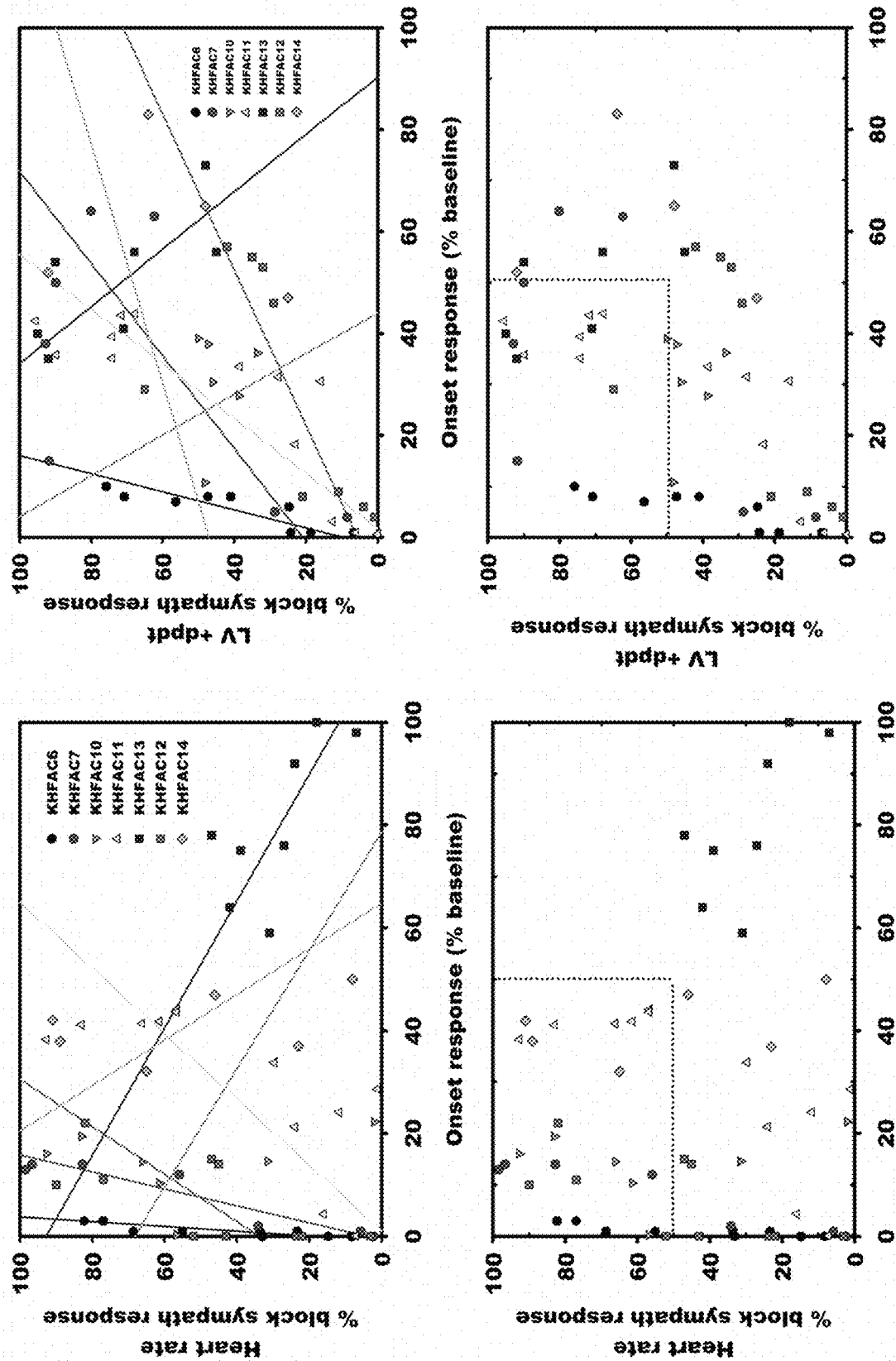

FIG. 8: Magnitude of onset does not directly relate to efficacy of block.

Figures 9A, 9B:
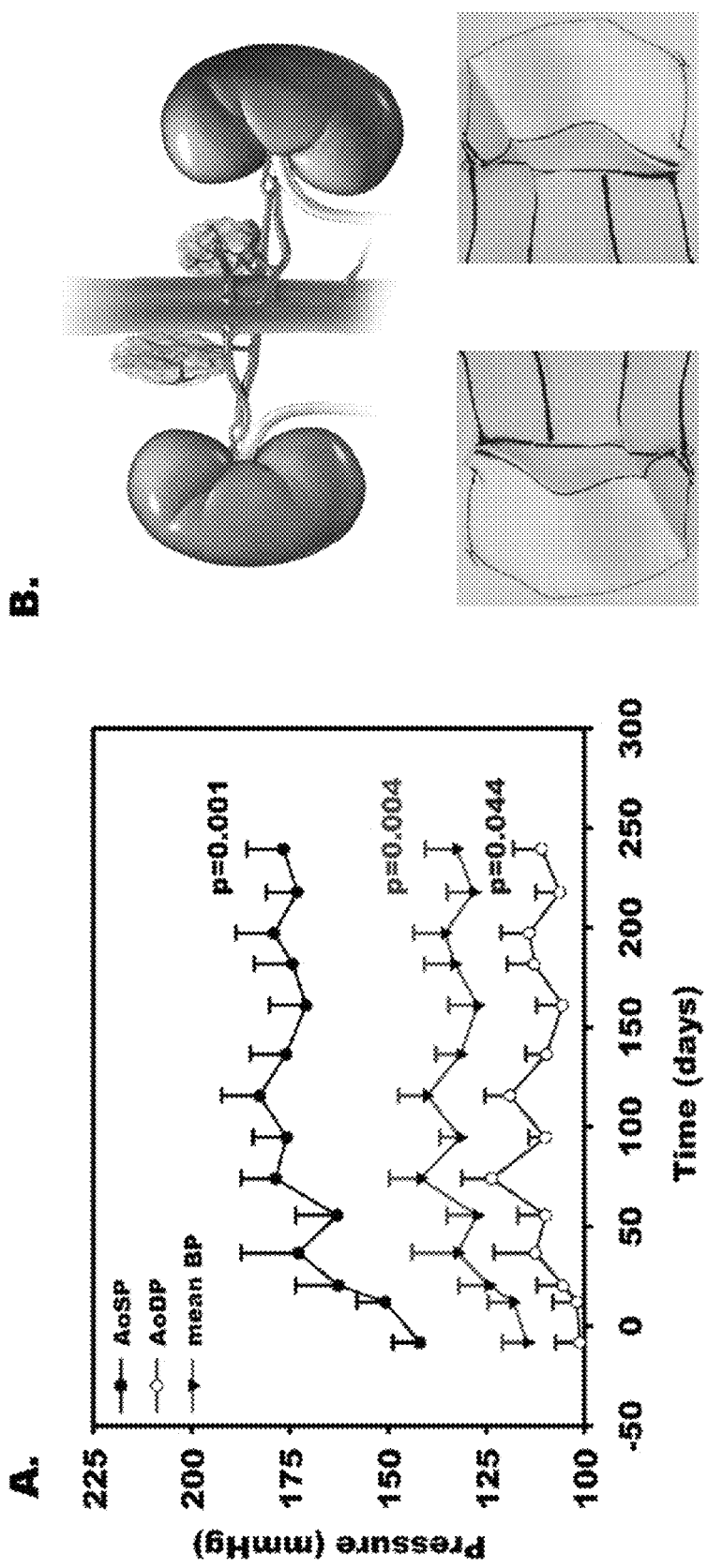

FIG. 9A-FIG. 9B depicts the results of experiments demonstrating that in adult canines, bilateral non-restrictive renal wrap (RW) induces chronic hypertension. At time zero, silk bags were loosely form/fit to surround both kidneys and the animals recovered from abdominal surgery; this being done without restricting renal blood flow.

Figure 10:
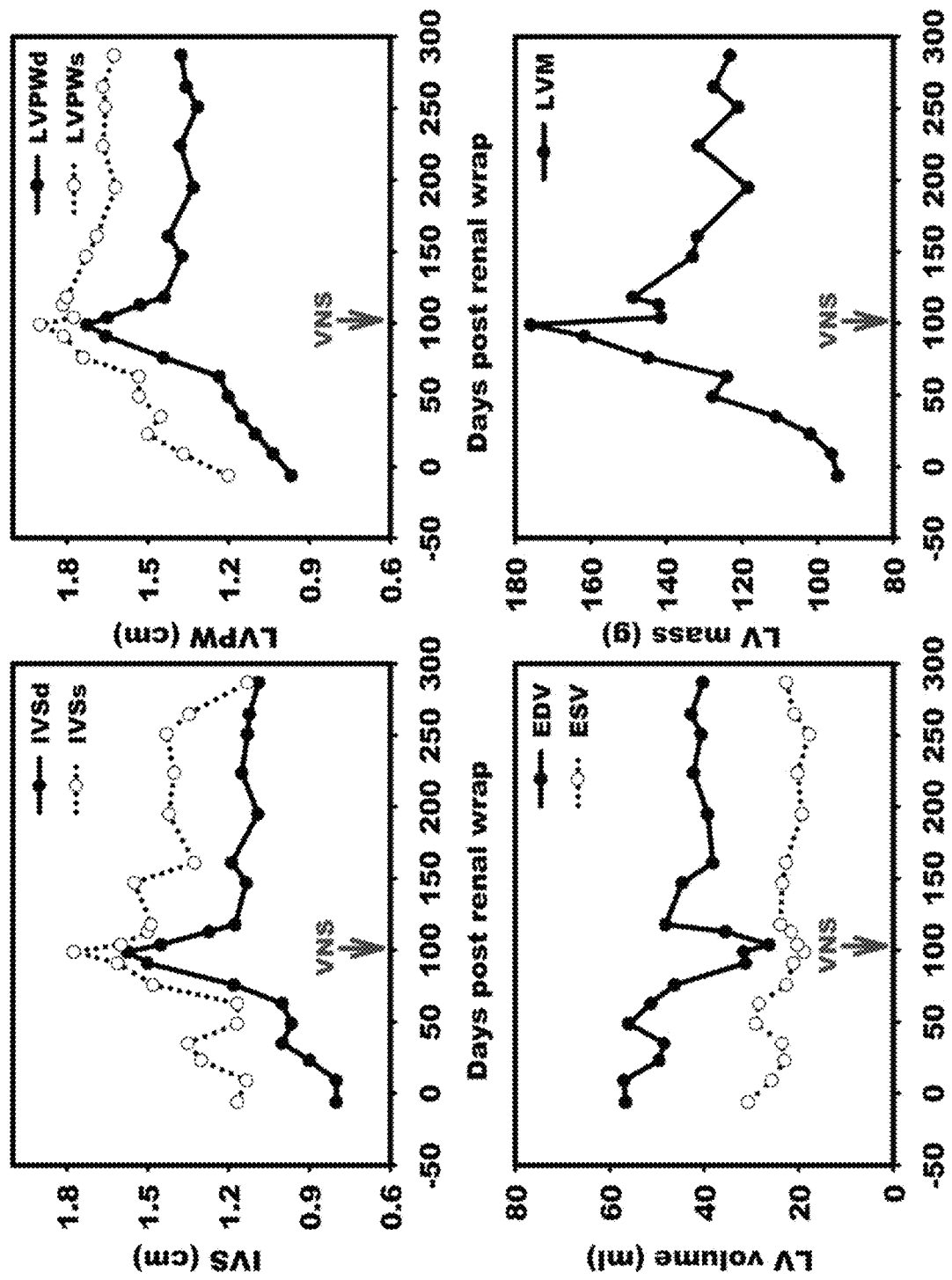
Figures 11A, 11B, 11C, 11D:
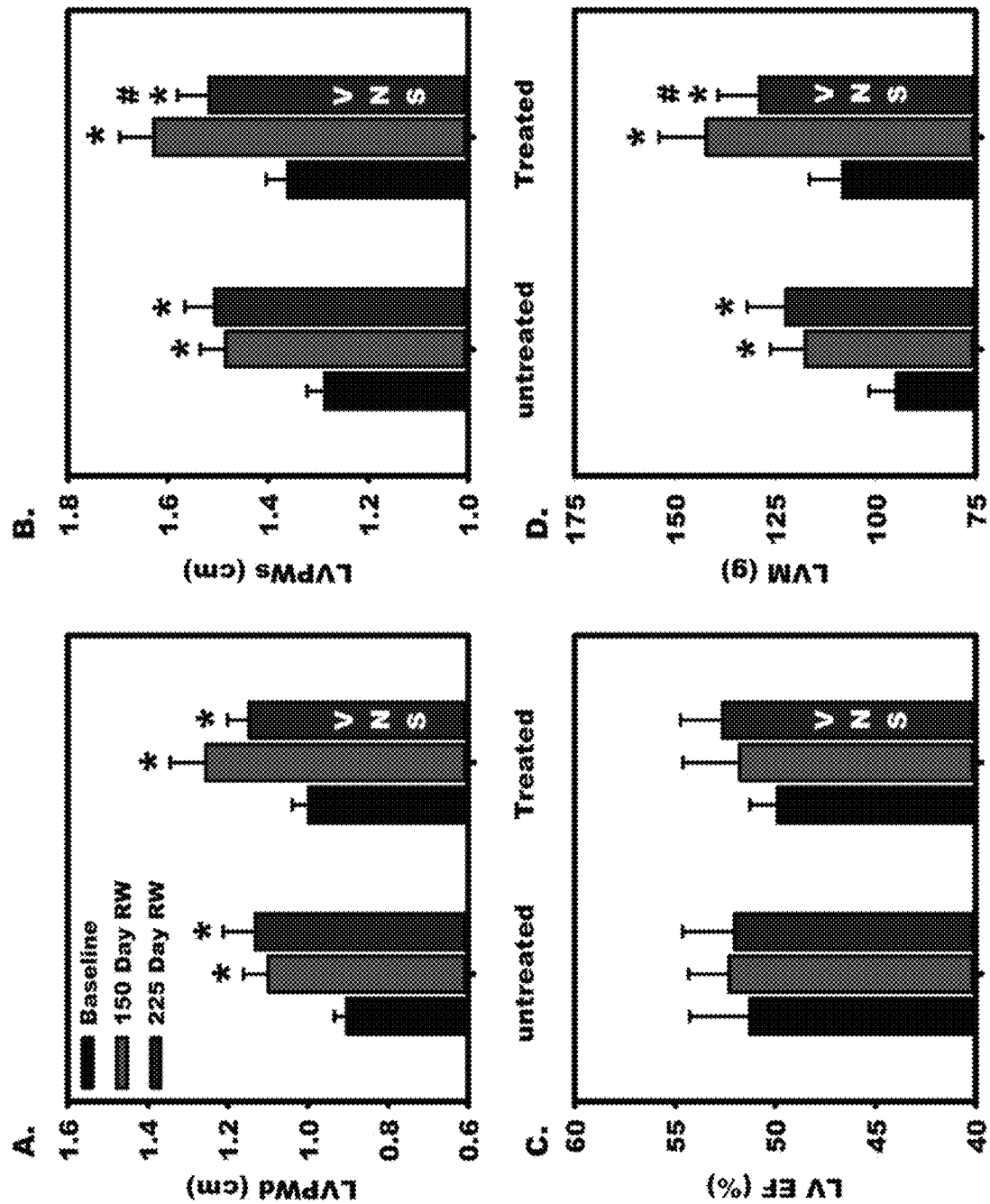

FIG. 10 depict representative changes in cardiac structure with chronic RW and effects of cervical vagal nerve stimulation (VNS) as delivered by an electrode wrapped around that nerve and connected to an implantable programmable generator (IPG) system implanted at day 99 and activated on day 102. IVS—interventricular septum thickness (in cm), LVPW—left ventricular posterior wall thickness (in cm), LV—left ventricle; d—diastolic; s—systolic. VNS delivered at 10 Hz, 250 μs duration, and with a 17.5% duty cycle (14 sec on, 66 sec off).

FIG. 11A-FIG. 11D depicts results of experiments which demonstrates that RW is a model of preserved ejection heart failure (HFpEF). Reactive cervical VNS reverse remodels the induced hypertrophy. LVPW—left ventricular posterior wall thickness; d—diastolic; s—systolic; LV EF—left ventricular ejection fraction; LVM—left ventricular mass *p<0.05 vs baseline; #p<0.05 vs 150 day RW.

Figures 12A, 12B, 12C, 12D:
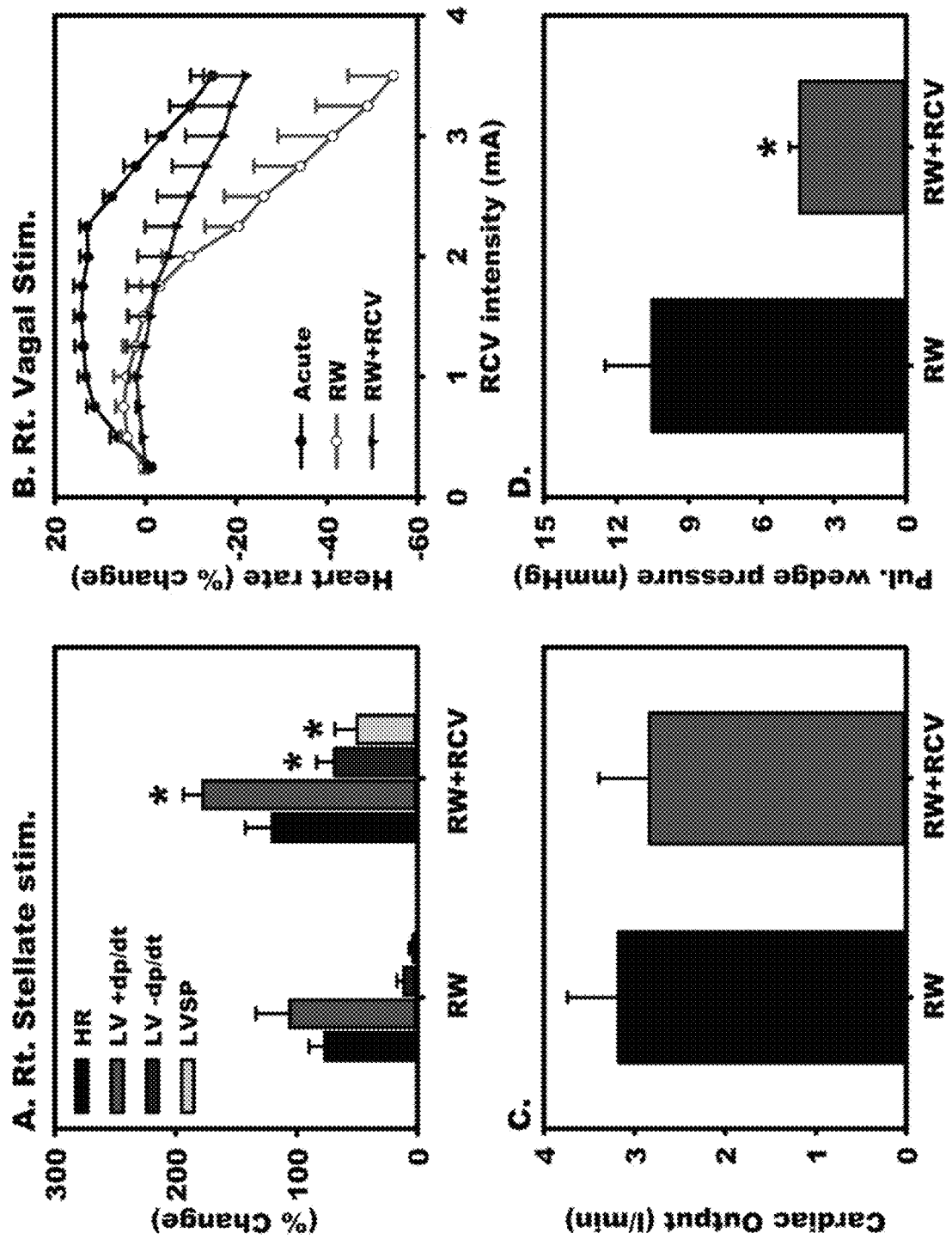

FIG. 12A-FIG. 12D depicts results of experiments demonstrating that VNS applied to right cervical vagus (RCV) preserves sympathetic function (FIG. 12A) and reverse remodels parasympathetic control towards normal levels (FIG. 12B); likewise reducing pulmonary wedge pressure (FIG. 12D) while preserving cardiac output (FIG. 12C). HR—heart rate; LV +dp/dt—left ventricular positive change in pressure per unit time; LV −dp/dt—negative change in LV pressure per unit time; Pul.—pulmonary. *p<0.05 RW vs. RW+VNS.

Figure 13:
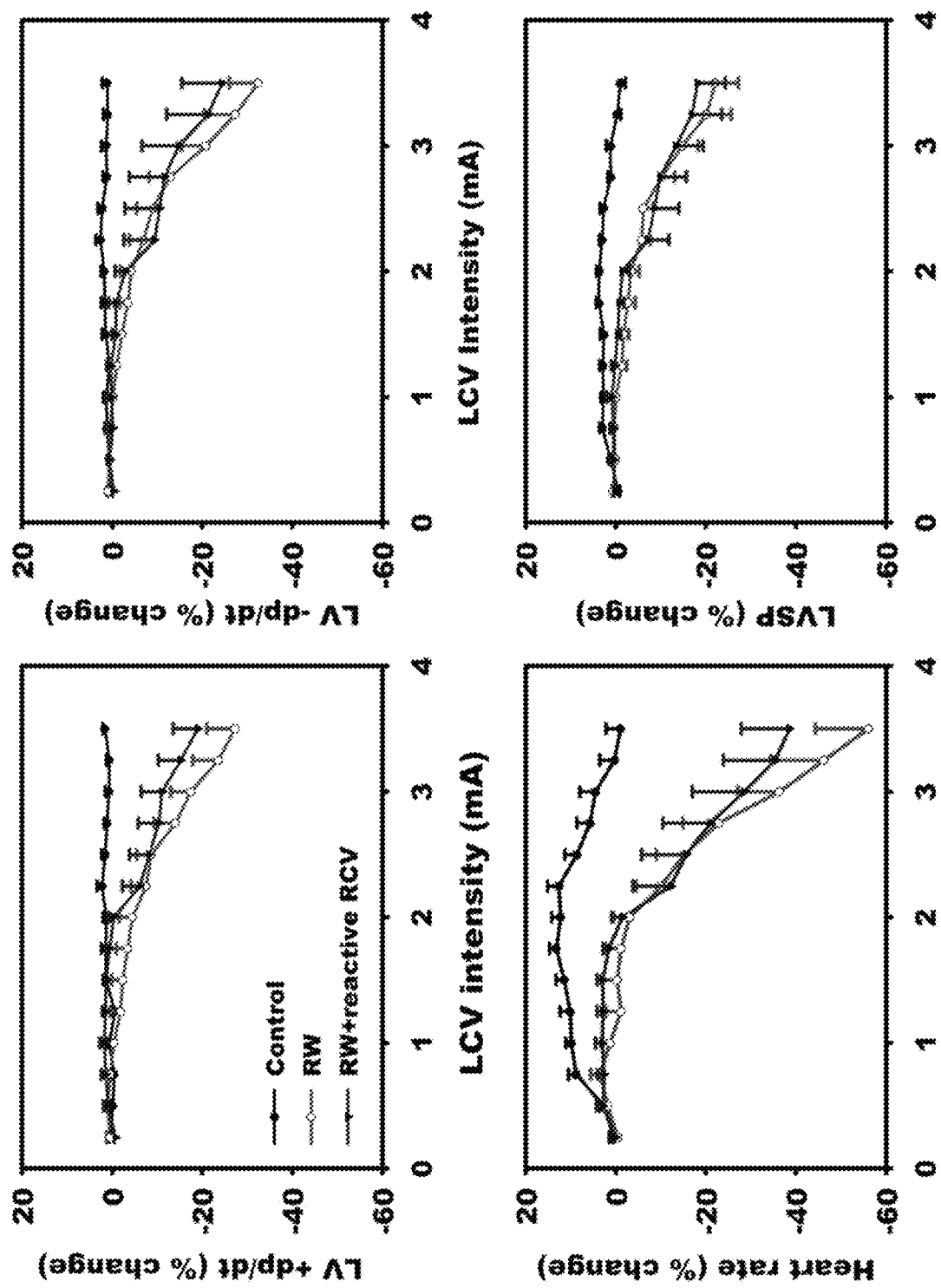
Figures 15A, 15B, 15C, 15D, 15E, 15F:
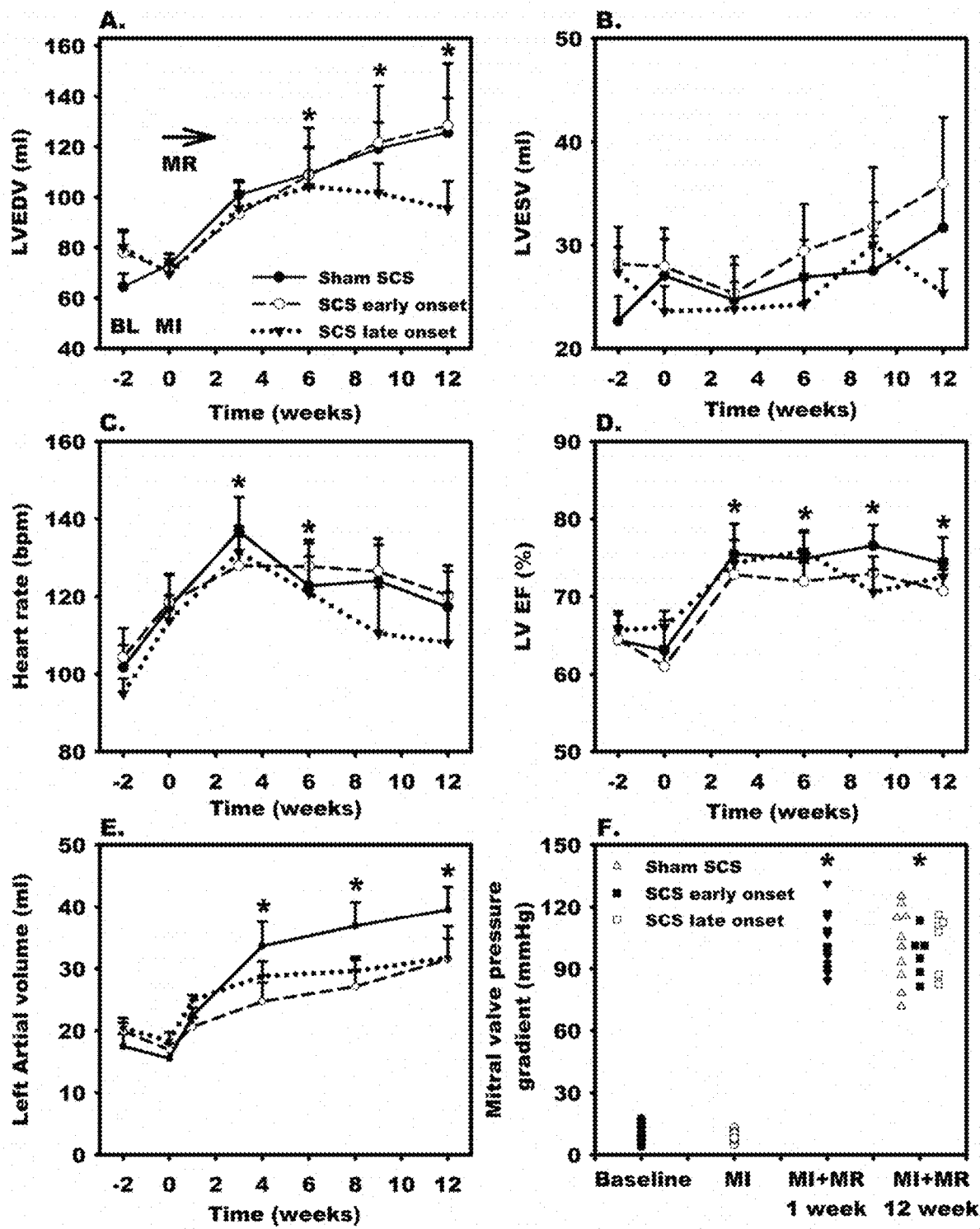

FIG. 13 depicts the results of experiments demonstrating that VNS applied to right cervical vagus (RCV) does not reverse remodel parasympathetic control exerted from the contralateral vagus. Rate of change in LV pressure defined in FIG. 12. LVSP—left ventricular systolic pressure.

FIG. 14 depicts a table depicting the raw data for various cardiac parameters obtained in control, RW, and RW+RCV treatment groups.

FIG. 15A-FIG. 15F depicts the results of example experiments demonstrating that spinal cord stimulation (SCS), delivered to the high thoracic (T1-T5) dorsal column's, minimally impacts cardiac remodeling post myocardial infarction (MI) with subsequent chronic mitral regurgitation (MR) induction. Induced changes in regional cardiac structure/function assessed by serial echocardiography. All animals had myocardial MI and then two weeks later MR induction. Shown are levels at baseline (BL), 2 weeks post MI (time 0 reading) and sequential assessments at 3 week intervals out to 12 weeks post MR induction. Groups are Sham SCS and animals treated with active SCS starting at 1 week (early onset SCS) or 6 weeks (late onset SCS) post-MR induction. Across all parameters shown (FIG. 15A=FIG. 15F), two way ANOVA showed no significant group effect, but with time significant effects (p<0.001) for all variables with exception of Left ventricular end systolic volume (LVESV, FIG. 15B), reflective of memory and plasticity. There were no significant differences between BL and MI in any variable shown. LVEDV—left ventricular end diastolic volume; LVEF—left ventricular ejection fraction. *p<0.02 from baseline.

Figure 16:
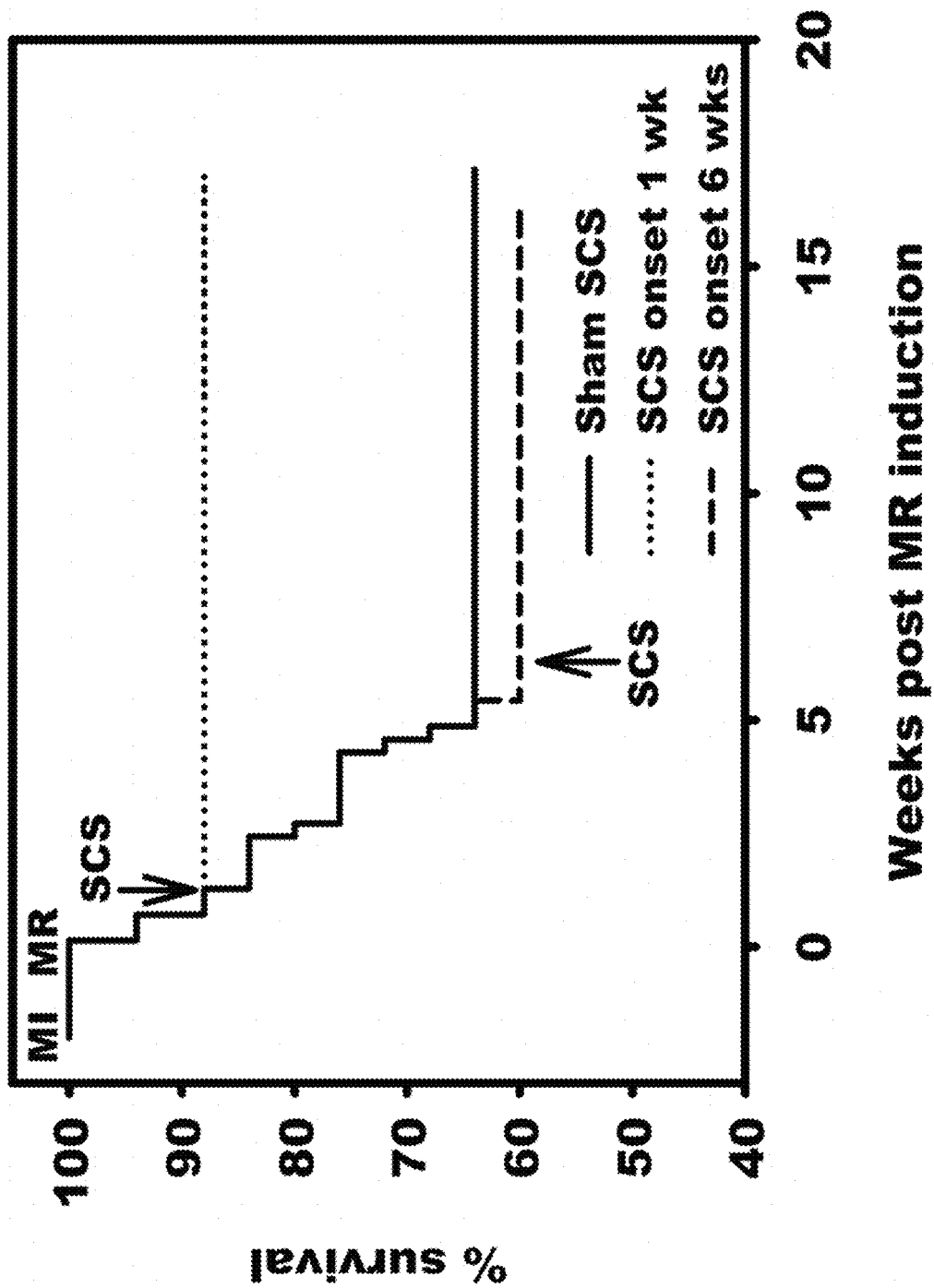
Figures 17A, 17B, 17C, 17D, 17E, 17F:
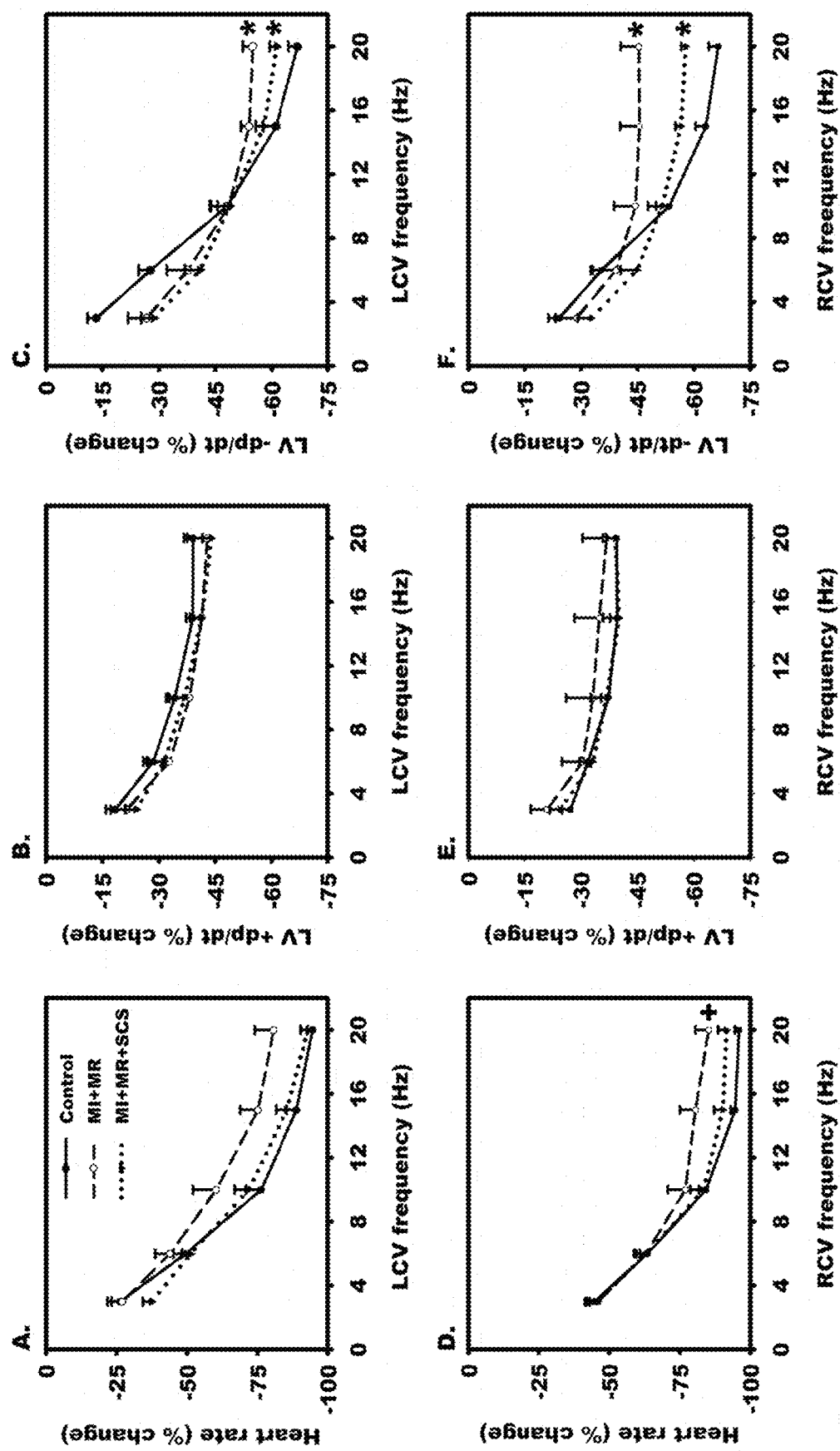

FIG. 16 depicts the results of experiments demonstrating that early onset SCS imparts a survival benefit in MI/MR model. Survival curves for the 32 animals all of which had SCS implants. All animals survived MI; MR was induced 2 weeks later. 18 animals received no active SCS, 7 animals had SCS initiated at 1 week post-MR induction and 7 had SCS initiated 6 weeks post-MR induction. One of 18 untreated animals was randomized to late onset SCS but died 3 days before treatment onset.

FIG. 17A-FIG. 17F depicts the results of experiments demonstrating that evoked changes in chronotropic (FIG. 17A and FIG. 17D) and left ventricular inotropic (FIG. 17B and FIG. 17E) and lusitropic (FIG. 17C and FIG. 17F) function in response to LCV (FIG. 17A-FIG. 17C) or RCV (FIG. 17D-FIG. 17F) bioelectric stimulation in control animals vs. animals with MI/MR with sham or active chronic SCS therapy. VNS was delivered at frequencies ranging from 3-20 Hz, 2× threshold, 500 μs pulse width for 14 s. Responses reflect % change from baseline during VNS as a function of stimulus intensity. *p<0.0001 vs control; +p<0.0025 vs control.

Figures 18A, 18B:
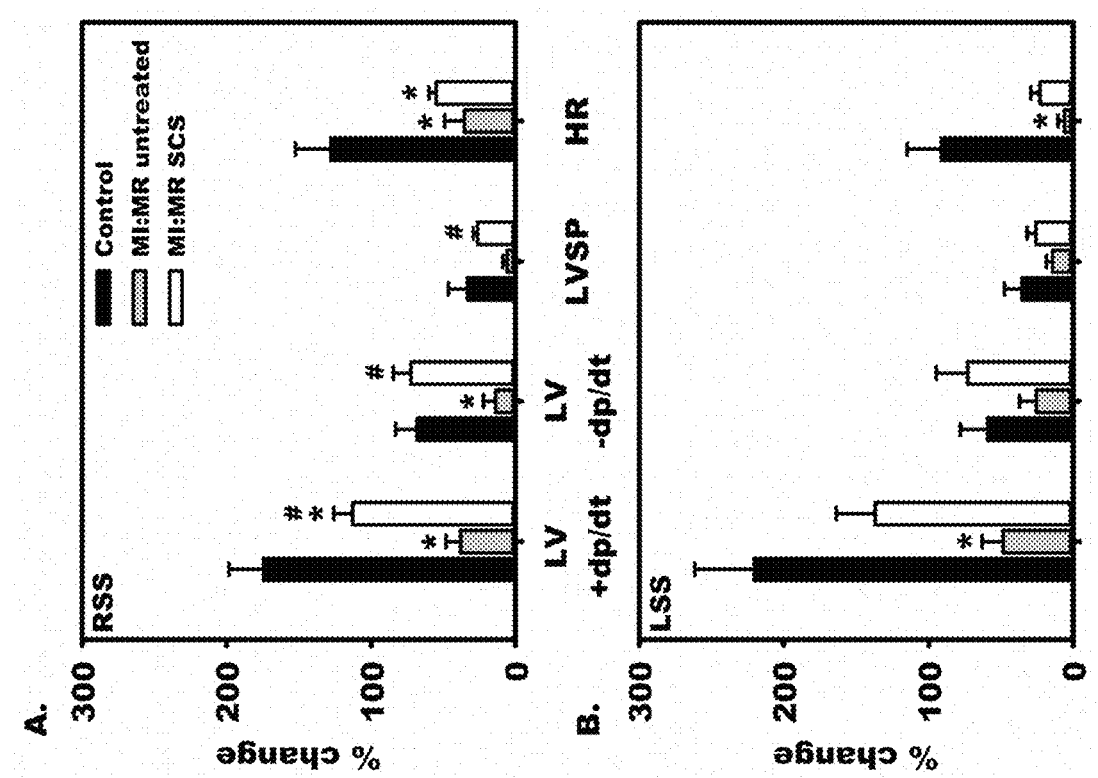

FIG. 18A-FIG. 18B depicts results of experiments demonstrating that evoked changes in left ventricular inotropic (LV +dp/dt) function, lusitropic (LV −dp/dt) function, systolic pressure (LVSP) and heart rate (HR) in response to right (RSS; FIG. 18A) and left (LSS: FIG. 18B) stellate electric stimulation in control animals vs animals with MI/MR with sham (untreated) or active SCS therapy. Stellate stimulation was delivered at 4 Hz, 1 ms pulse width, at an intensity of 3× threshold for 1 min. *p<0.02 from control; #p<0.05 MI/MR untreated vs active SCS treatment.

Figures 19A, 19B:
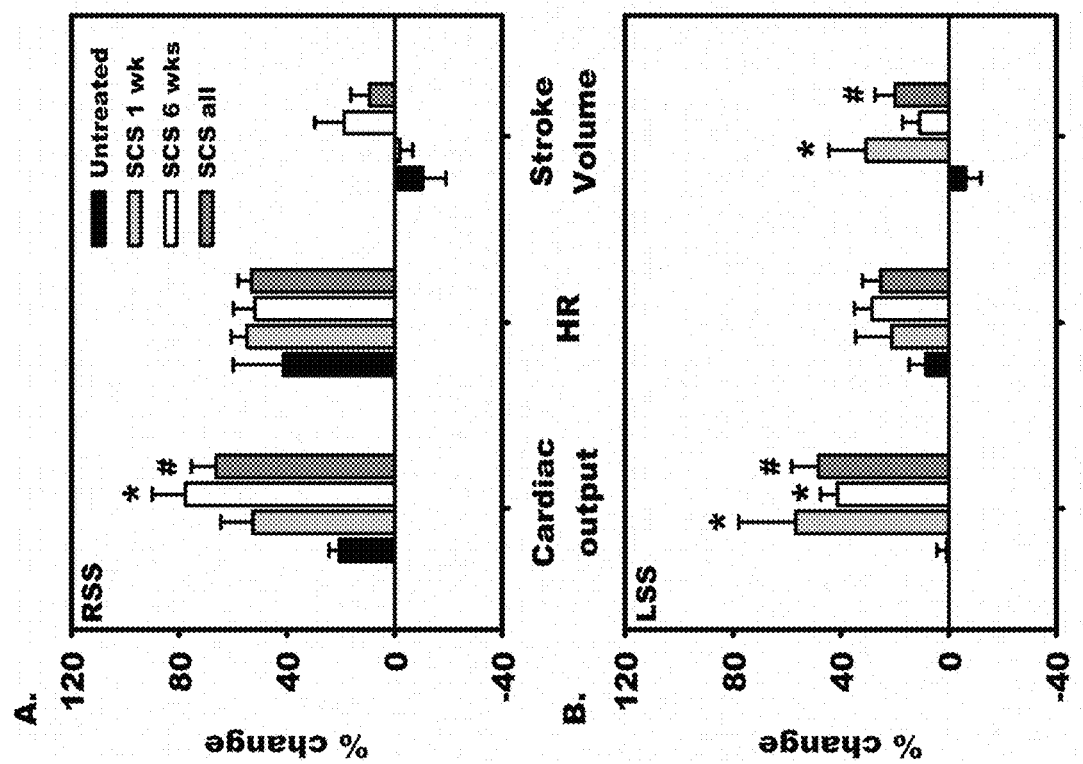

FIG. 19A-FIG. 19B depicts the results of example experiments demonstrating that SCS augments cardiac output reserve in response to sympathetic stimulation in setting of chronic myocardial ischemia/mitral regurgitation. Shown are % changes from baseline for cardiac output, and its constituent parts heart rate and stroke volume, in response stellate electric stimulation in animals with MI/MR with sham (untreated) or active SCS therapy. Stellate stimulation was delivered at 4 Hz, 1 ms pulse width at an intensity of 3× threshold for 1 min. Cardiac output assessed by thermal dilution via swan ganz catheter placed in pulmonary artery. SCS groups presented as early (1 week), late (6 weeks) or combined (all). *p<0.05 untreated vs early or late onset SCS; #p<0.05 untreated vs all SCS.

Figure 20:
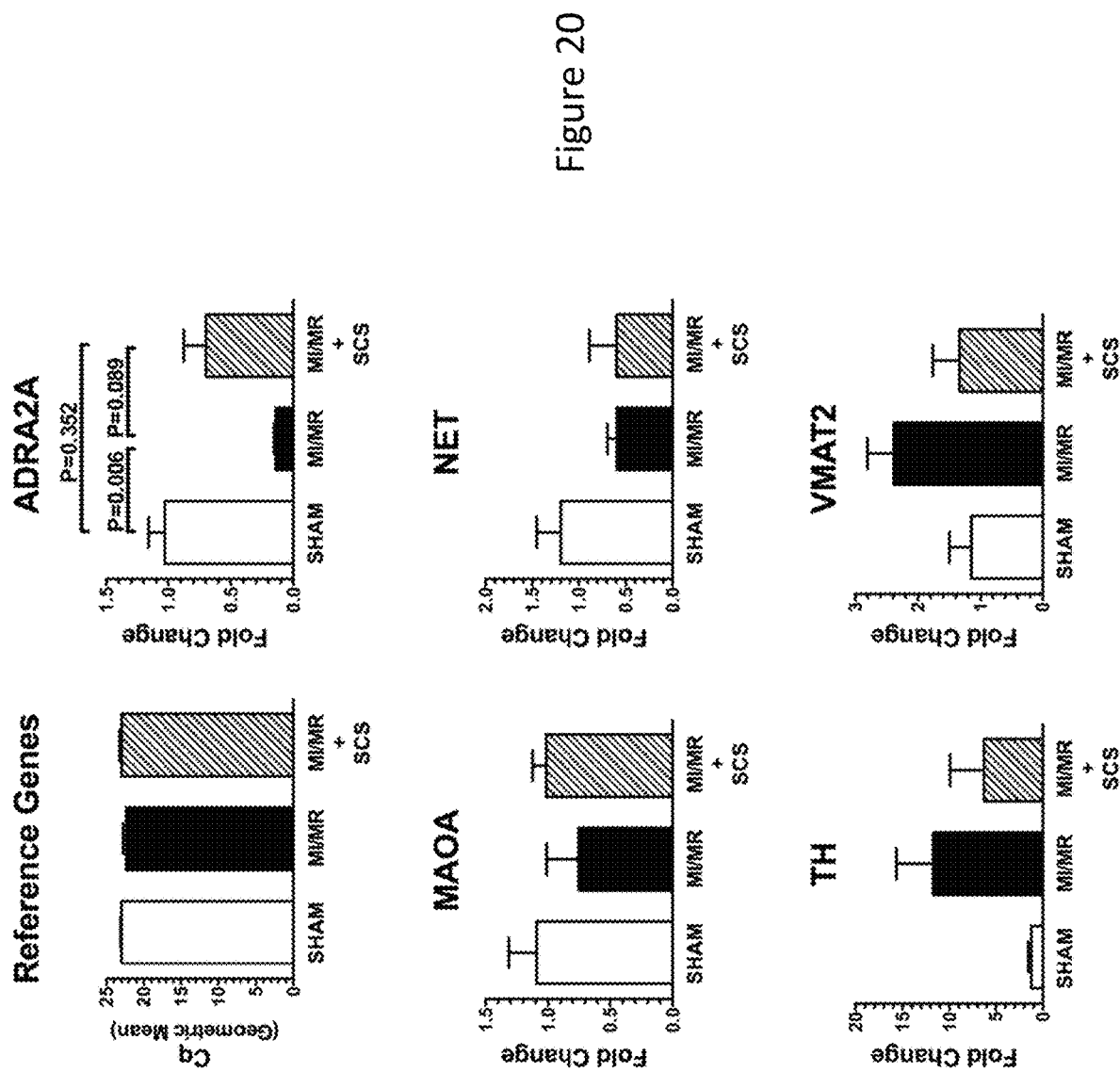

FIG. 20 depicts the results of experiments demonstrating relative expression levels of catecholamine-related genes of interest in dog stellate ganglia from sham control animals (SHAM; n=6) compared to those with chronic mitral regurgitation/myocardial infarction (MI/MR; n=3) and chronic MI/MR with spinal cord stimulation (MI/MR+SCS; n=4). The upper left panel shows the geometric means Cq of reference genes (TATA box binding protein, beta-2 microglobulin). Remaining panels show the relative abundance in fold change of indicated gene transcripts: ADRA2A=alpha-2A adrenergic receptor; MAOA=monoamine oxidase A; NET=norepinephrine transporter; TH=tyrosine hydroxylase; VMAT2=vesicular monoamine transporter-2. Statistically significant differences between groups are indicated above bars. Shown are the means±SEM of fold changes computed by comparing treatment groups to the SHAM group. Only group comparisons of ADRA2A expression levels demonstrated statistical significance; lines over bars show p values of group comparisons for these gene.

Figure 4:
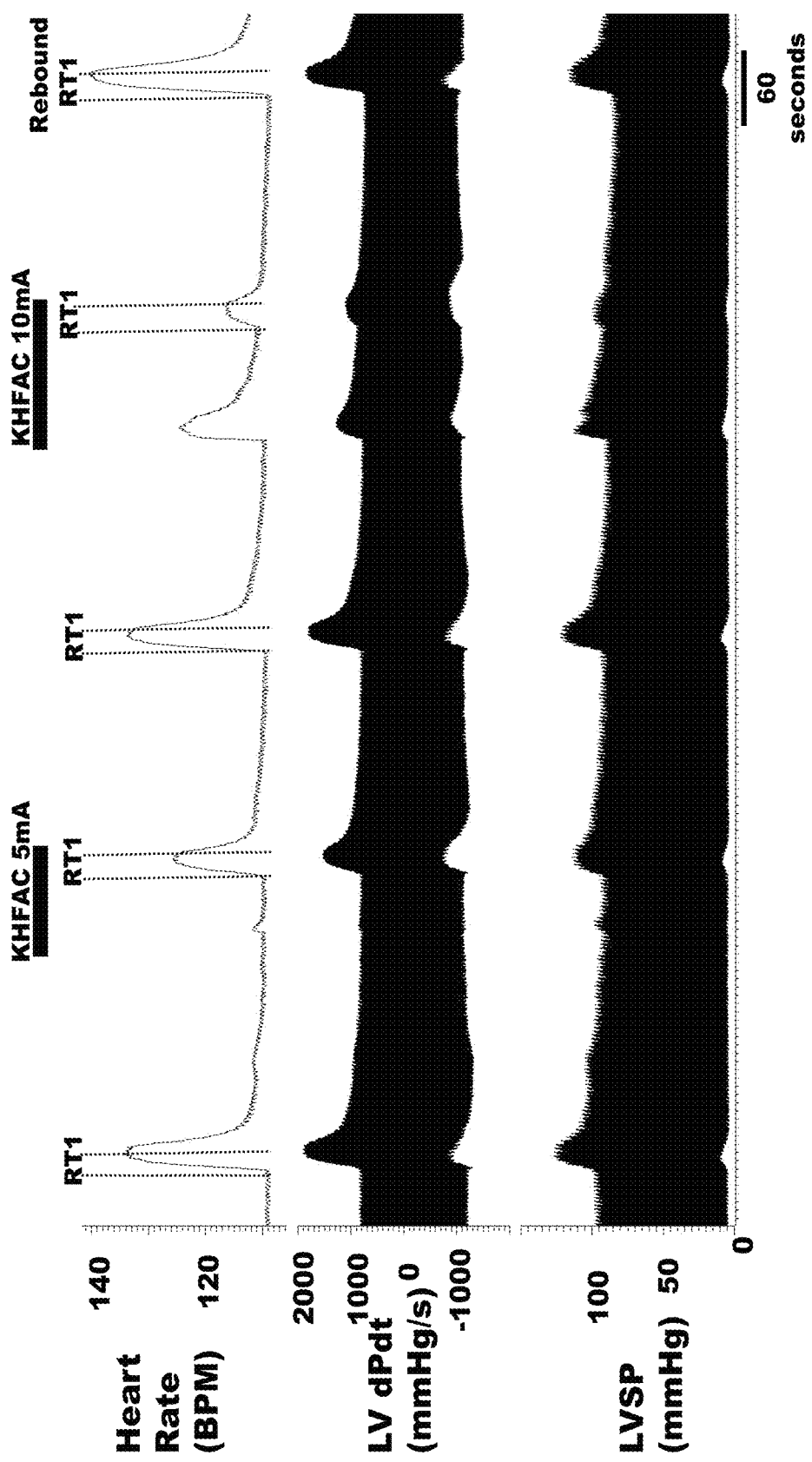
FIG. 4: Effects of KHFAC at varying currents on cardiac sympathetic responses to stellate (RT1) stimulation. RT1 stimulation is performed at baseline and after each KHFAC to evaluate recovery. KHFAC was delivered at 20 kHz. At 5 mA note the small onset response and ~40% decrease in RT1 evoked cardiac responses. At 10 mA, the onset response was more evident at the onset of KHFAC and the blocking efficacy improved to ~75%. Also note the rebound phase of the T1 stimulation post KHFAC with an augmented response for heart rate (HR) and left ventricular dP/dt (LV dPdt) after the higher intensity KHFAC.
Figures 21A, 21B, 21C, 21D:
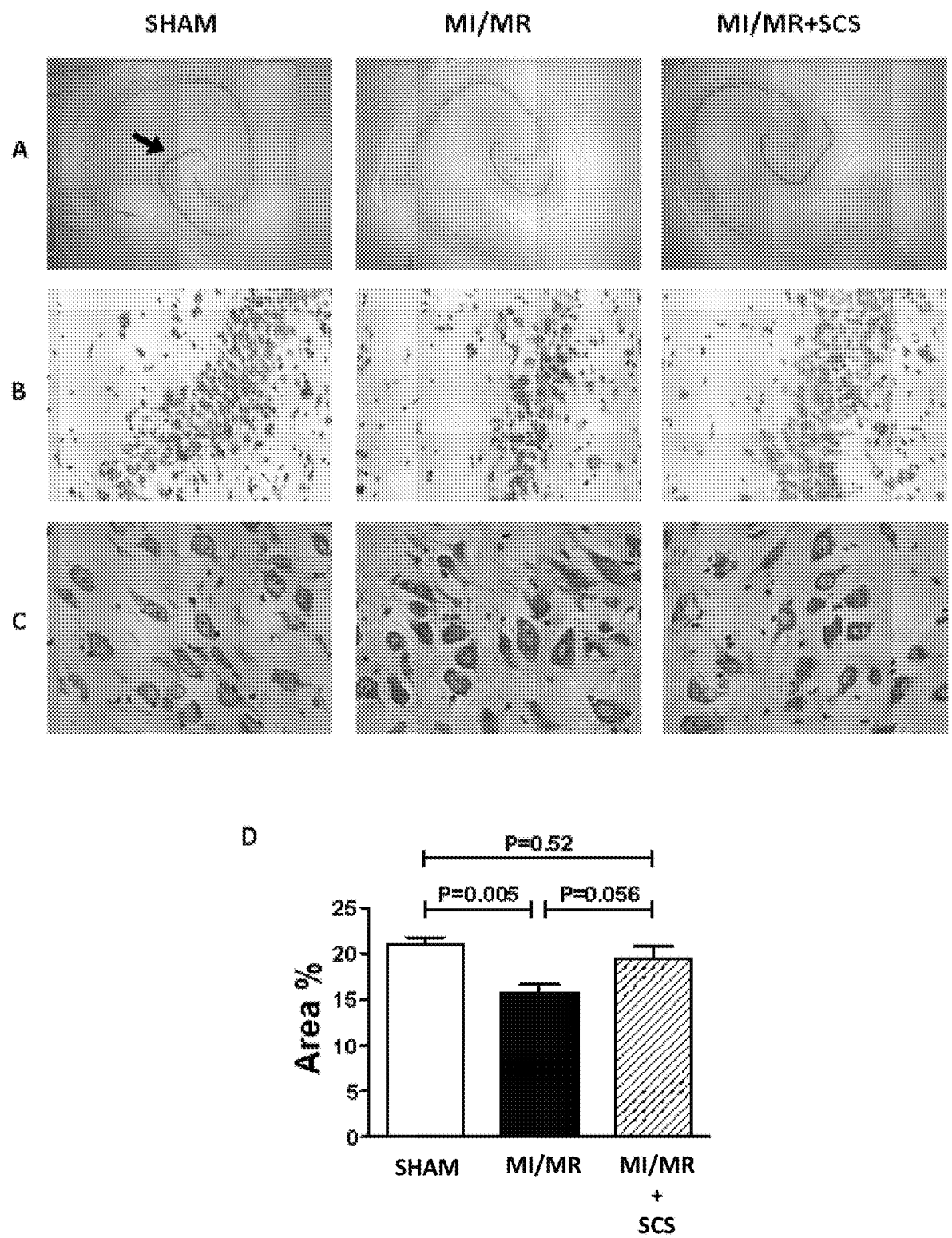

FIG. 21A-FIG. 21D depicts the results of experiments demonstrating the effect of chronic mitral regurgitation/myocardial infarction (MI/MR) and spinal cord stimulation (SCS) on canine hippocampal morphology. Shown are representative coronal sections of post-fixed, paraffin-embedded, and Nissl-stained canine hippocampus from the three treatment groups of dogs (FIG. 21A, 4× view of whole hippocampus; FIG. 21B, 20× view of granular layer of the dentate gyrus; FIG. 21C, 40× view of CA3 neurons). Dentate gyms neuronal densities estimated by measuring fractional areas occupied by neurons in the dentate gyrus are shown in FIG. 21D. Lines over bars show p values of designated group comparisons.

Figures 22A, 22B, 22C:
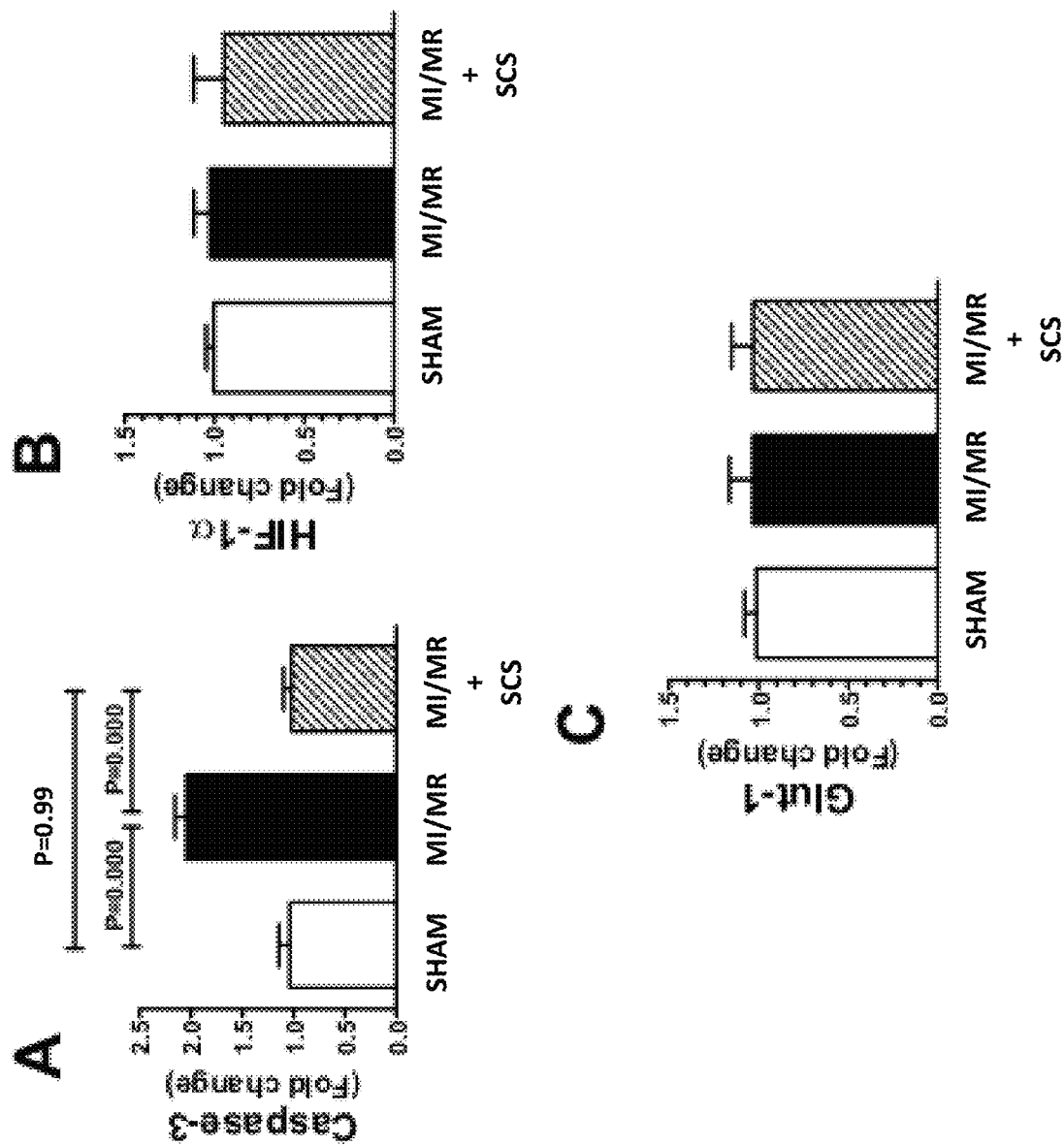

FIG. 22A-FIG. 22C depicts the results of experiments demonstrating relative gene expression of caspase-3 (FIG. 22A), HIF-1α (FIG. 22B) and Glut-1 (FIG. 22C) in the hippocampus from sham operated control (SHAM; n=8-9), chronic mitral regurgitation/myocardial infarction (MI/MR; n=8) and chronic MI/MR treated with spinal cord stimulation (MI/MR+SCS; n=6): Shown are the means±SEM of fold changes computed comparing treatment groups to the SHAM group. Only group comparisons of caspase-3 expression levels demonstrated statistical significance; lines over bars show p values of group comparisons for this gene.

FIG. 23 depicts a table depicting primer sequences used.

FIG. 24 depicts the results of experiments showing the hemodynamic profile of animals at baseline, in response MI and then MR induction 2 weeks later, and at termination. Termination data shown based on intervention received: sham SCS (untreated), early SCS (started 1 week post MR induction) and late SCS (started 6 weeks post MR induction). Terminations were done at 14-16 week post MR induction. *p≤0.05 from baseline 1 or baseline 2; +p≤0.05 Baseline 1 vs Baseline 2; #p≤0.05 from baseline 1.

FIG. 25 depicts the results of experiments examining the expression of vascular biomarkers indicative of cardiac stress/damage in response to MI and then to MR induction 2 weeks later, and at termination. Blood sample obtained immediately prior to MI induction (baseline), at 2 and 14 days after MI induction, and at 2 day and 16 weeks post MR induction. *p≤0.05 from baseline; +p≤0.05 from 2 day post-MI; #p≤0.05 from 14 day post-MI (and just prior to MR induction).

FIG. 26. A schematic depicting changes in plasticity and memory described herein.

DETAILED DESCRIPTION

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present invention provides compositions, devices, systems, and methods for monitoring and modulating cardiac function and dysfunction in a subject. For example, in certain aspects, the present invention provides for modulation of the autonomic nervous system to alter the plasticity and/or memory of the autonomic network. For example, the present invention is related to methods and devices for delivering energy to the autonomic nervous system to alter the memory and/or plasticity of the autonomic nervous system.

In one embodiment, the present invention provides a method of altering the memory and/or plasticity of the autonomic network. Neural network plasticity is defined as structural adaptations of the cardiac nervous system to changing physiological/pathophysiological conditions and/or delivery of energy from an external source. Neural network memory is defined as functional adaptation of the cardiac nervous system due to integration of historical and current information in response to changing physiological/pathophysiological conditions and/or delivery of energy from an external source.

Memory and plasticity are interdependent processes in neural network function, including that exerted by the cardiac nervous system for control of cardiac function. With appropriate neuromodulation therapy, autonomic control of the heart can brought closer to normal levels, and the potential for fatal arrhythmias is reduced (Ardell et al, 2016, J Physiol 594:3877-3909; Shivkumar et al., 2016, J Physiol 594: 3911-3954). With appropriate neuromodulation therapy, by targeting and mitigating the cardiac diseased induced adverse remodeling of the cardiac nervous system, the progression of heart failure can be slowed (Premchand, et al, 2016, J. Card Fail 22: 639-642; Beaumont et al, 2016, Am J Physiol Heart Circ Physiol 310:H1349-H1359).

In one embodiment, the method comprises delivering energy to an autonomic neural structure (e.g., ganglion or nerve), such that the energy alters the neural structure plasticity during and beyond the acute stimulation/energy delivery period, with effects that extend beyond the ganglion or nerve itself to the greater autonomic network. In certain embodiments, the delivered energy can be in the form of electrical, electromagnetic, acoustic, thermal, or the like. In certain embodiments, the method comprises placing one or more electrodes directly in or adjacent to that neural structure by direct surgical access or vascular access. In one embodiment, the one or more electrodes are placed in proximity to the neural structure wherein the neural structure is the intrinsic cardiac nervous system. In certain embodiments, the neural structure is the intrathoracic nerve trunk, cervical vagosympathetic nerve trunk, the paravertebral sympathetic chain ganglia, the dorsal root ganglia, nodose ganglia, petrosal ganglia, the spinal cord, or the peripheral distributions of the 9th and 10th and 12th cranial nerves. In certain embodiments, the method produces an altered neural network structure that includes changes in one or more of changes in: neuronal apoptosis potential, neural network interconnectivity, neuronal phenotype, neurotransmitter release, receptors and the neural-myocyte interface. In one embodiment, the neural structure that is altered is the neural structure to which energy is delivered. In one embodiment, the neural structure that is altered is remote from the neural structure to which energy is delivered. For example, the method can alter the neural structure of one or more structures that are rostral and/or caudal to the stimulation site. In one embodiment, the energy is delivered acutely. In one embodiment, the energy is delivered chronically.

In one embodiment, the present invention provides a method for altering the function of neural structure. In one embodiment, the method comprises delivering energy to an autonomic neural structure (e.g., ganglion or nerve), such that the energy alters its function during and beyond the stimulation/energy delivery period, with effects that extend beyond the ganglion or nerve itself to the greater autonomic network. In certain embodiments, the delivered energy can be in the form of electrical, electromagnetic, acoustic, thermal, or the like. In certain embodiments, the method comprises placing one or more electrodes directly in or adjacent to that neural structure by direct surgical access or vascular access. In one embodiment, the one or more electrodes are placed in proximity to the neural structure wherein the neural structure is the intrinsic cardiac nervous system. In certain embodiments, the neural structure is the intrathoracic nerve trunk, cervical vagosympathetic nerve trunk, the paravertebral sympathetic chain ganglia, the petrosal or nodose ganglia, the dorsal root ganglia, the spinal cord, or the peripheral distributions of the 9th and 10th and 12th cranial nerves.

In certain embodiments, the altered neural network function includes changes in one or more of: neural activity, network interconnectivity, and altered neurotransmitter release at the neural-myocyte interface. In one embodiment, the altered neuronal function is in a subset or subsets of neurons contained within intrathoracic ganglia including afferents, local circuit, sympathetic or parasympathetic soma; and/or in primary cardiovascular afferents associated with the dorsal root, petrosal or nodose ganglia and their projections to brainstem and spinal cord neural networks.

In one embodiment, the present invention provides a method to alter cardiac autonomic neural network structure and/or function (i.e., plasticity and/or memory), comprising inserting into or placing adjacent to an electrode(s) on a nerve or ganglia and delivering energy to that structure and the energy is delivered in open-loop by external control.

In one embodiment, the present invention provides a method to alter cardiac autonomic neural network structure and/or function (i.e., plasticity and/or memory), comprising inserting into or placing adjacent to an electrode(s) on a nerve or ganglia and delivering energy to that structure and the energy is delivered in a closed-loop system or method. For example, in certain embodiments, the delivery of energy is triggered by one or more signals recorded or detected by the closed-loop system. In one embodiment, the signal controlling application of energy is the identification of a neural signature or recordings indicative of adverse autonomic activity, which can be recorded from electrodes placed into or on intrathoracic ganglia or intrathoracic axonal projections. In one embodiment, the signal used for controlling application and output of energy is the identification of a neural signature or recordings indicative of adverse cardiovascular activity, which can be recorded from electrodes placed into or on nodose, petrosal or dorsal root ganglia. In one embodiment, the signal used for controlling application and output of energy is the identification of a neural signature or recordings indicative of adverse autonomic activity, which can be recorded from electrodes placed into or on the cervical vagosympathetic nerve trunk. In one embodiment, the signal used for controlling application and output of energy is identification of adverse autonomic activity as recorded from a chemical sensor placed into or onto the heart. In one embodiment, the signal used for application and output of energy is identification of adverse neurohumoral activity as recorded by a chemical sensor placed in the vascular space including but not limited to the great vessels leading to and from the heart, coronary vasculature or the chambers of the heart.

In one embodiment, the method comprises providing energy, (e.g. an electrical stimulus) to the vagus nerve, which thereby alters the memory and/or plasticity of the autonomic network. In certain embodiments, the method comprises providing an electrical stimulation to the cervical vagosympathetic nerve trunk, intrathoracic vagosympathetic nerve trunk, or the auricular branch of the vagus nerve.

In one embodiment, the method comprises providing an electrical stimulus that increases activity in the vagus nerve. In one embodiment, the method comprises providing an electrical stimulus that inhibits or decreases activity the vagus nerve. In one embodiment, the method comprises contacting one or more stimulating electrodes to the vagus nerve and applying vagus nerve stimulation (VNS). In certain embodiments, VNS can be applied to modulate parasympathetic autonomic activity, and treat or prevent cardiac dysfunction. In one embodiment, VNS is applied at about 1 Hz-50 Hz. In one embodiment, VNS is applied at about 5 Hz-30 Hz. In one embodiment, VNS is applied at about 5 Hz-10 Hz. In one embodiment, VNS is applied at about 10 Hz-20 Hz. In one embodiment, VNS is applied with a pulse width of about 0.1-1000 µs. In one embodiment, VNS is applied with a pulse width of about 1-500 µs. In one embodiment, VNS is applied with a pulse width of about 100-500 µs. In one embodiment, VNS is applied with a pulse width of about 250-500 µs. In one embodiment, VNS is applied with a pulse width of about 130 µs.

In one embodiment, VNS is applied with a current of about 0.1-10 mA. In one embodiment, VNS is applied with a current of about 0.5-5 mA. In one embodiment, VNS is applied with a current of about 1-2 mA. In one embodiment, VNS is applied with a current of about 0.6-3.5 mA.

In one embodiment, the method comprises providing energy (e.g., an electrical stimulus) to the spinal cord, which thereby alters the memory and/or plasticity of the autonomic network. In certain embodiments, the method comprises providing an electrical stimulation to the T1-T5 dorsal column of the spinal cord or the C1-C2 dorsal column of the spinal cord.

In one embodiment, the method comprises providing an electrical stimulus that increases activity in the spinal cord. In one embodiment, the method comprises providing an electrical stimulus that inhibits or decreases activity the spinal cord.

In one embodiment, the method comprises contacting one or more stimulating electrodes to the spinal cord and applying spinal cord stimulation (SCS). In certain embodiments, SCS can be applied to modulate parasympathetic autonomic activity, and treat or prevent cardiac dysfunction.

In one embodiment, SCS is applied at about 1 Hz-100 Hz. In one embodiment, SCS is applied at about 5 Hz-75 Hz. In one embodiment, SCS is applied at about 10 Hz-50 Hz.

In one embodiment, SCS is applied with a pulse width of about 0.1-1000 µs. In one embodiment, SCS is applied with a pulse width of about 1-500 µs. In one embodiment, SCS is applied with a pulse width of about 100-500 µs.

In one embodiment, SCS is applied with a current of about 0.1-10 mA. In one embodiment, SCS is applied with a current of about 0.5-5 mA. In one embodiment, SCS is applied with a current of about 1-2 mA.

In one embodiment, the method comprises decreasing activity in a nerve by administering high frequency alternating current (HFAC) or kilohertz frequency alternating current (KHFAC) to a nerve or ganglion of the autonomic nervous system, which thereby alters the memory and/or plasticity of the autonomic network.

In one embodiment, KHFAC is applied at about 5 kHz-30 kHz. In one embodiment, KHFAC is applied at about 10 kHz-25 kHz. In one embodiment, KHFAC is applied at about 15 kHz-20 kHz.

In one embodiment, KHFAC is applied at a voltage of about 5-30 volts. In one embodiment, KHFAC is applied at a voltage of about 10-25 volts. In one embodiment, KHFAC is applied at a voltage of about 15-20 volts.

In certain embodiments, modulation of the autonomic nervous system, as described herein, is triggered by a signal derived from the monitoring of cardiac autonomic activity, cardiac electrical activity, or the cardiac interstitial chemical milieu. For example, in certain aspects, the method comprise detecting a signal, pattern, or signature indicative of the need for therapeutic intervention; and modulating the memory and/or plasticity of the autonomic network, as described herein.

In certain embodiments, the method comprises delivering energy to produce a scalable block of efferent projecting axons to the heart. The energy for producing a scalable block can include, for example, electrical energy, electromagnetic energy, acoustic energy, and thermal energy. In some embodiments, the method comprise monitoring or evaluating block efficacy, which can be done manually or in a closed loop fashion, where evoked changes in neural signals or cardiac signs are the sensory detect signal against which block efficacy is assessed.

In certain embodiments, the invention comprises a method of monitoring cardiac autonomic activity. For example, in certain aspects, the method comprises measuring the activity of one or more of: intrinsic cardiac nervous system (ICNS), local circuit neurons (LCNs), atrial intrinsic cardiac ganglia, ventricular intrinsic cardiac ganglia, nodose ganglia, mediastinal ganglia, middle cervical ganglia, stellate ganglia, and dorsal root ganglia. For example, in certain embodiments, the method comprises contacting, placing, or inserting one or more recording electrodes at one or more recording sites, including, but not limited to, intrinsic cardiac nervous system (ICNS), local circuit neurons (LCNs), atrial intrinsic cardiac ganglia, ventricular intrinsic cardiac ganglia, ventral interventricular ganglionated plexus (VIV GP), dorsal interventricular glanglionated plexus (DIV GP), inferior vena cava-inferior atrial ganglionated plexus (IVC-IA GP), right marginal artery ganglionated plexus, right atrial ganglionated plexus, nodose ganglia, petrosal, mediastinal ganglia, middle cervical ganglia, stellate ganglia, and dorsal root ganglia.

In certain embodiments, the method comprises monitoring cardiac electrical activity. For example, in certain embodiments, the method comprises contacting, placing or inserting one or more recording electrodes on or in a location of the heart, including but not limited to atrial epicardial surface, atrial endocardial surface, ventricular epicardial surface, ventricular endocardial surface. In certain embodiments, the method comprises inserting electrodes into the myocardial wall within the atria or ventricles.

In certain embodiments, the method comprises monitoring multi-pole cardioneural function by measuring cardiac electrical activity and autonomic neural activity. For example, in certain embodiments, the method comprises contacting, placing, or inserting one or more recording electrodes on or in a location of the heart; and contacting, placing, or inserting one or more electrodes at one or more non-cardiac muscle recording sites, including, but not limited to, intrinsic cardiac nervous system (ICNS), local circuit neurons (LCNs), atrial intrinsic cardiac ganglia, ventricular intrinsic cardiac ganglia, nodose ganglia, petrosal ganglia, mediastinal ganglia, middle cervical ganglia, stellate ganglia, and dorsal root ganglia.

The recording electrode(s) may be any suitable type and size electrode for detecting electrical signals in the heart or autonomic nervous system. Exemplary electrodes include, but are not limited to, single shank electrodes, 2D multi-shank electrodes, 3D multi-shank electrodes, and multielectrode arrays. In one embodiment, the method comprises the use of an implantable or partially implantable sensor incorporating a plurality of electrodes for detecting electrical signals. For example, in one embodiment, the sensor comprises a linear microelectrode array (LMA). In certain embodiments, the LMA comprises a plurality of electrodes. For example, in one embodiment, the LMA comprises 16 platinum/iridium electrodes. The electrodes may be placed at their desired recording sites using any suitable method, including, but not limited to, vascular access, epicardial access, and surgical access.

In certain embodiments, the method comprises monitoring the cardiac electrical activity and/or cardiac autonomic activity under basal or resting conditions. In certain aspects, the method comprises monitoring the cardiac electric activity and/or cardiac autonomic activity as the subject carries on day to day tasks, including, but not limited to, sleeping, eating, working, walking, and the like. In certain aspects, the method comprises monitoring the cardiac electric activity and/or cardiac autonomic activity in response to a stimulus, including but not limited to, exercise, epicardial mechanical stimulation, endocardial mechanical stimulation, changes in preload or afterload, thermal stress, orthostatic stress, mental stress, electrical stimulation of the sympathetic nervous system, electrical stimulation of the parasympathetic nervous system, administration of a biologic or chemical treatment, or the like.

In certain embodiments, the method comprises monitoring activity for a given duration to detect a pattern of activity or to detect the presence or frequency of abnormal activity. In certain aspects, the monitored or measured activity can be referred to as a neural signature. The neural signature may be indicative of cardiac function or dysfunction, or the risk of cardiac dysfunction. In one exemplary embodiment, a monitored neural signature may be compared to a baseline or reference signature. Baseline or reference neural signatures may be patient specific, or they may be collective or pooled data representative of average values for subjects having at least one characteristic in common. Exemplary characteristics may include patient gender, age, activity level, diet, congenital defect, genetic trait, metabolic status, and the like. In certain embodiments, the baseline or reference neural signature is defined with respect to one or more cardiovascular stressors, including, but not limited to, exercise, orthostatic stress, temperature, Valsalva maneuver, and spirometry test. After establishing a baseline or reference neural signature representative of a healthy state, subsequent measurements of cardiac electrical activity and/or cardiac autonomic activity are taken to establish a real-time neural signature for comparison to the baseline or reference, such that a determination can be made as to whether the subject is in need of a treatment.

As contemplated herein, the neural signature may include one or more parameters, including without limitation, parameters relating to spontaneous firing rate, activity during cardiac cycle phases, temporal relationships between neurons, response to mechanosensitive input, change in cardiac loading conditions, response to epicardial pacing, chemoreceptor and nociceptive input. For each parameter, a threshold value may be established that is indicative of a subject in need of a treatment, or of a particular type of treatment. In certain embodiments, exceeding only one threshold value may be determinative of a need for treatment and/or type of treatment, whereas in other embodiments, multiple threshold values may be exceeded in order to be determinative of a need for treatment, or particular type of treatment. In still other embodiments, a scoring algorithm may be used to determine whether the differences in neural signature comparisons is demonstrative of a need for treatment, or of a particular type of treatment. In certain embodiments, scoring includes changes in individual or grouped activity, directionality of changes in such activity and temporal relationships between 2 or more neurons The method may be used to diagnose a cardiac condition, assess the recovery of a cardiac condition, assess the efficacy of a therapy of a cardiac condition, determine the likelihood of a future cardiac event, or determine that a prior cardiac event has occurred.

Exemplary cardiac conditions or events detected or monitored by way of the presently described method includes, but is not limited to ischemic heart disease, myocardial infarction, premature ventricular contraction, arrhythmia, reduced ejection heart failure, preserved ejection heart failure, atrial bradycardia, atrial tachycardia, atrial fibrillation, ventricular tachycardia, and the like.

In one aspect, the present invention provides a system for modulation of the autonomic nervous system, as described herein, to modulate the memory and/or plasticity of the autonomic network. In certain embodiments, the system of the invention comprises one or more components to stimulate the autonomic nervous system, for example at the vagus nerve, spinal cord, paravertebral chain or other autonomic nervous system input.

In certain embodiments, the system comprises one or more stimulatory electrodes to apply an electrical signal. Exemplary electrodes include cuff electrodes, needle electrodes, flat interface electrodes, intrafasicular electrodes, glass suction electrodes, paddle electrodes, bipolar hemicuff electrodes, bipolar hook electrodes, percutaneous cylindrical electrodes, and the like. The electrodes may be monopolar, bipolar, tripolar, quaripolar, or having five or more poles. The electrodes may be fabricated from, or be partially or entirely coated with, a high charge capacity material such as platinum black, iridium oxide, titanium nitride, tantalum, poly(elthylenedioxythiophene) and suitable combinations thereof. An electrode suited for delivery of HFAC or KHFAC is described in U.S. Patent Publication US2011/0125216.

In certain embodiments, the system comprises one or more pulse generators coupled to one or more electrodes to provide electrical stimulation. The pulse generators may be implantable or external to the subject.

In one embodiment, the system comprises one or more pacing electrodes suitable for application of cardiac electrical stimulation at one or more epicardial or endocardial sites.

In certain embodiments, the system is a closed-loop system comprising one or more recording electrodes and one or more stimulating electrodes. In one embodiment, the system comprises a control unit that receives input from the recording electrodes and delivers input to the stimulating electrodes. For example, in certain embodiments, the recording electrodes detect a signal or signals, the control unit processes the signal or signals to determine the activity or pattern of activity at the recording site, and, when applicable, the control unit communicates with the stimulating electrodes to deliver a stimulus.

The system may include at least one recording electrode, including, but not limited to, single shank electrodes, 2D multi-shank electrodes, 3D multi-shank electrodes, and multielectrode arrays, to monitor electrical signals. In one embodiment, the system comprises an implantable or partially implantable sensor incorporating a plurality of electrodes for detecting electrical signals. For example, in one embodiment, the sensor comprises a linear microelectrode array (LMA). In certain embodiments, the LMA comprises a plurality of electrodes. For example, in one embodiment, the LMA comprises 16 platinum/iridium electrodes. In one embodiment, the LMA comprises multiple shank electrodes in 2D or 3D configurations. The sensor may comprise any suitable type and size of electrode suitable for detecting electrical signals.

These electrodes may be designed for insertion into (or to make contact with) the nerves or ganglia of a subject to effectively detect electrical activity of the neurons for recording at a control unit connected to the electrodes. While the electrodes are implantable in a subject, the control unit may either be implantable in the subject or external to the subject, as desired.

In one embodiment, the system may comprise one or more pre-amplifiers, amplifiers, or filters to process the detected electrical signal. Such components may be positioned on an implanted sensor, or alternatively be present on external hardware. For example, in one embodiment, the preamplifier provides for low and high pass filtering with gain control. In one embodiment, the filtering range is 300 to 3 KHz with gain up to 5K. In certain embodiments, the filtering range and/or gain of the preamplifier is adjustable to optimize signal to noise ratio. In one embodiment, the preamplifier and control device allow for transient blocking of input signal as related to electrical stimuli or electrical activity generated by atrial or ventricular tissues.

In one embodiment, the system comprises one or more components for producing scalable block of efferent projecting axons to the heart. For example, in certain embodiments, the system comprises one or more components for producing scalable block of efferent projecting axons to the heart are configured for delivering energy for producing the scalable block, wherein the energy is selected from the group consisting of electrical energy, electromagnetic energy, acoustic energy, and thermal energy.

In certain aspects, the system comprises one or more stimulating electrodes, as described herein, placed dorsal to and used in conjunction with the one or more components for producing scalable block of efferent projecting axons to the heart.

In one embodiment, the system comprises components for measuring or evaluating the block efficacy. For example, in one embodiment, evaluating of block efficacy is done manually. In one embodiment, evaluating of block efficacy is done in close looped fashion and evoked changes in neural signals or cardiac signals are the sensory detect signal against which block efficacy is assessed.

In one embodiment, the system comprises an implantable or external control unit, which may be powered by any method understood in the art, including a standard battery, standard wiring for external power transfer, or it may include a receiver coil for wireless power transfer. The control unit may include a microprocessor and any form of memory for storing control software and any received and/or processed data. The control unit may further include a transmitter and receiver or any hardware and software necessary for transmitting and/or receiving data with an external processing unit for further analysis of the recorded activity within each neuron being measured. The external processing unit may be one or more computing units, and may be or include any type of computing device including a desktop laptop, tablet, smartphone or other wireless digital/cellular phones, wrist watches, televisions or other thin client device as would be understood by those skilled in the art. Generally, any computing devices described herein may include at least one processor, standard input and output devices, as well as all hardware and software typically found on computing devices for storing data and running programs, and for sending and receiving data over a network, if needed. It should also be appreciated that the recorded data may be further filtered, amplified or any other type of additional processing for analyzing and displaying the data as desired by the external processing unit or other connected computing device within the system.

The system may further include a software platform with a graphical user interface (GUI) for modulating the function of the one or more sensors, pulse generators, and/or electrodes and for displaying information regarding the historical or real-time electrical activity of the measured neurons or ganglia, as well as historical or real-time measurement of the subject's cardiac function. In certain embodiments, the wireless communication information transfer to and from the sensor control unit and the external processing unit may be via a wide area network and may form part of any suitable networked system understood by those having ordinary skill in the art for communication of data to additional computing devices, such as, for example, an open, wide area network (e.g., the internet), an electronic network, an optical network, a wireless network, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, the external processing unit may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for telemetric data transfer from the sensor control unit to the external processing unit, and vice versa. For example, data transfer can be made via any wireless communication and may include any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the sensor control unit and external processing unit via systems described above.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. Exemplary GUIs of the invention may include the ability for a user to control the function or mode of the sensors, as well as the ability to display individual cardiac-related neuron activity, pooled data of neuronal activity, or of general cardiac function as would be understood by those skilled in the art. Such data may include indices of network function including, but not limited to, temporal relationships of neural activity to one another, temporal relationships to cardiac electrical or mechanical events, temporal relationships to controlled events including pacing, mechanical, or chemical stressors. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed folder files, or other layering techniques understood by those skilled in the art.

The software may also include standard reporting mechanisms, such as generating a printable results report, or an electronic results report that can be transmitted to any communicatively connected computing device, such as a generated email message, text or file attachment. Likewise, particular results of the aforementioned system can trigger an alert signal, such as the generation of an alert email, text or phone call, to alert a patient, doctor, nurse, emergency medical technicians, or other health care provider of the particular results.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: KHFAC-Induced Persistence, Memory and Plasticity

Experiments were conducted to examine the effects of KHFAC on changes in the persistence, plasticity and memory of the autonomic nervous system. The KHFAC stimulation method is depicted in FIG. 1A. Bipolar KHFAC electrodes were deployed to region between 1st and 2nd paravertebral ganglia or to the dorsal and ventral ansae subclavia (FIG. 1A). Sympathetic efferent projections to the heart were activated at either the 2nd paravertebral (T2) or stellate ganglia (T1) respectively and the blocking efficacy of KHFAC evaluated.

Figure 2:
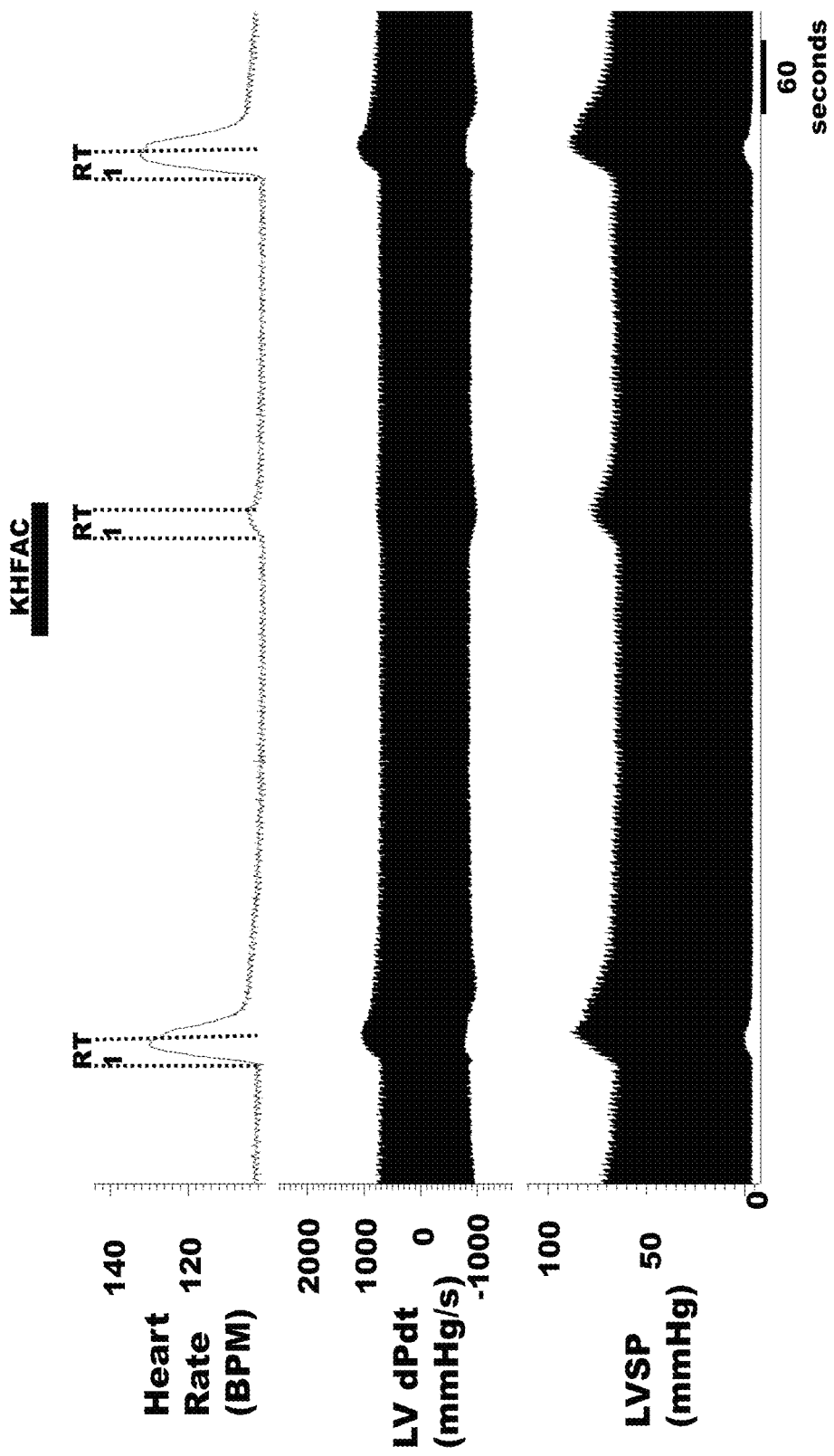
FIG. 2: Preemptive KHFAC. Cardiac responses to sympathetic efferent activation (right T1 stimulation; RT1) before, during KHFAC (30 KHz 10 mA), and post KHFAC. KHFAC applied to dorsal and ventral ansae subclavia. The responses shown represent bioelectonic stimulation (RT1 or KHFAC) evoked changes in heart rate (HR), left ventricular dP/dt (LV dPdt), and left ventricular systolic pressure (LVSP). This KHFAC demonstrates no onset response, near complete suppression of the cardiac response to right paravertebral stimulation at the T1 level (RT1; aka stellate ganglia) and full recovery of the RT1 stimulation hemodynamic response post KFHAC.

The effects of preemptive KHFAC is shown in FIG. 2. Sympathetic efferent evoked cardiac response before, during KHFAC (30 KHz 10 mA), and post KHFAC. KHFAC applied to dorsal and ventral ansae subclavia. The responses shown represent bioelectronic stimulation (RT1 or KHFAC) evoked changes in heart rate (HR), left ventricular dPdt (LV dP/dt), and left ventricular systolic pressure (LVSP). This KHFAC demonstrates no onset response, near complete suppression of the cardiac response to right paravertebral stimulation at the T1 level (RT1; aka stellate ganglia) and full recovery of the RT1 stimulation hemodynamic response post KFHAC.

Figure 3:
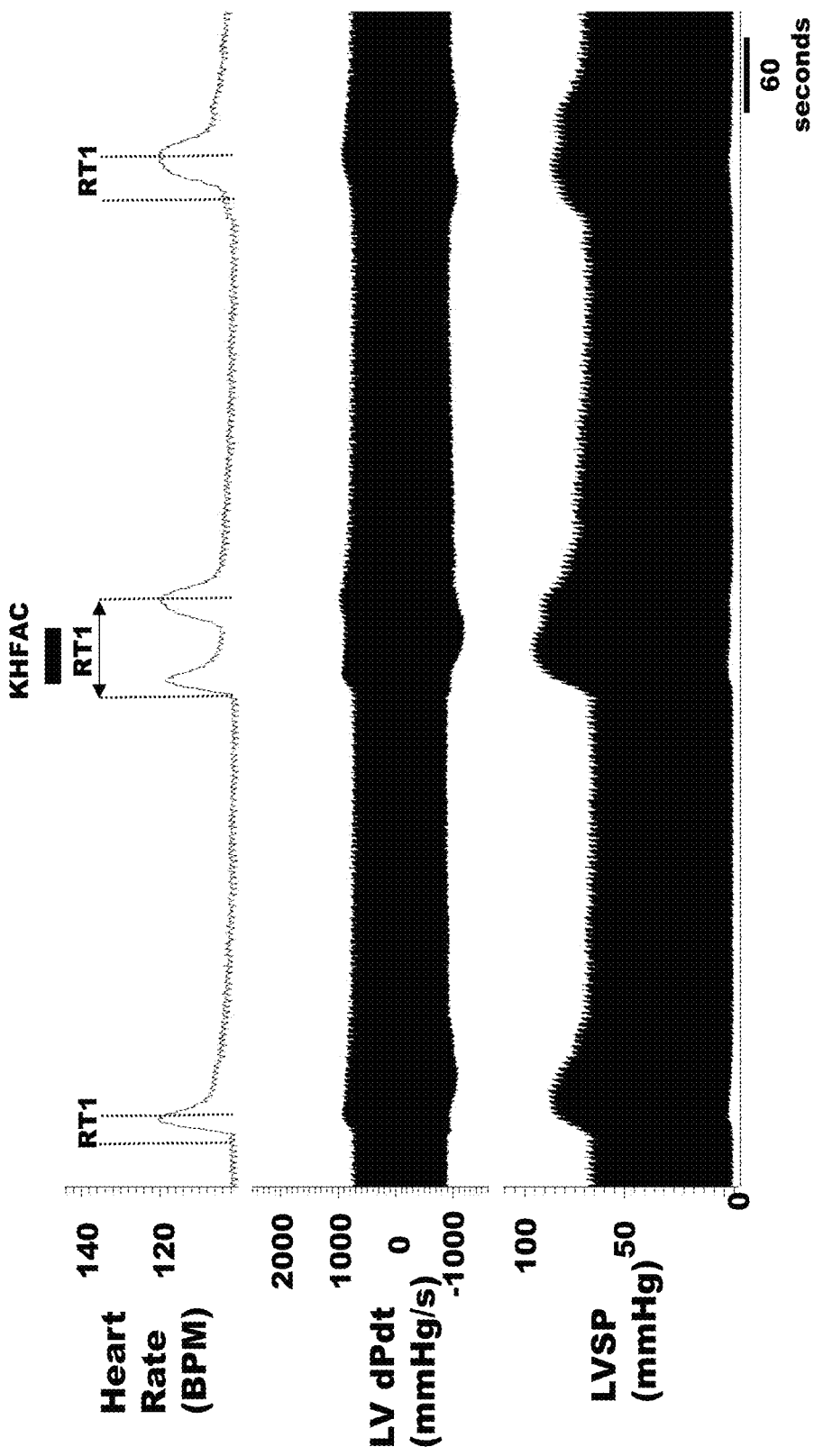
FIG. 3: Reactive KHFAC. KHFAC applied reactively during RT1 stimulation effectively reduces cardiac responses (heart rate, dP/dt) to sympathetic activation with rapid recovery of the RT1 evoked response post KHFAC.

The effects of reactive KHFAC are shown in FIG. 3. KHFAC applied reactively during RT1 stimulation effectively reduces the evoked cardiac augmentation (heart rate, dP/dt) with rapid recovery of the RT1 evoked response post KHFAC.

Experiments were also conducted to evaluate the effects of KHFAC at varying currents on the sympathetic-evoked cardiac responses to stellate (RT1) stimulation. RT1 stimulation is performed at baseline and after each KHFAC to evaluate recovery. KHFAC was delivered at 20 kHz. At 5 mA note the small onset response and ~40% decrease in RT1 evoked cardiac responses. At 10 mA, the onset response was more evident and the blocking efficacy improved to ~75%. Also note the rebound phase of the T1 stimulation post KHFAC with an augmented response for heart rate (HR) and left ventricular dPdt (LV dP/dt) after the higher intensity KHFAC.

Figures 5A, 5B, 5C:
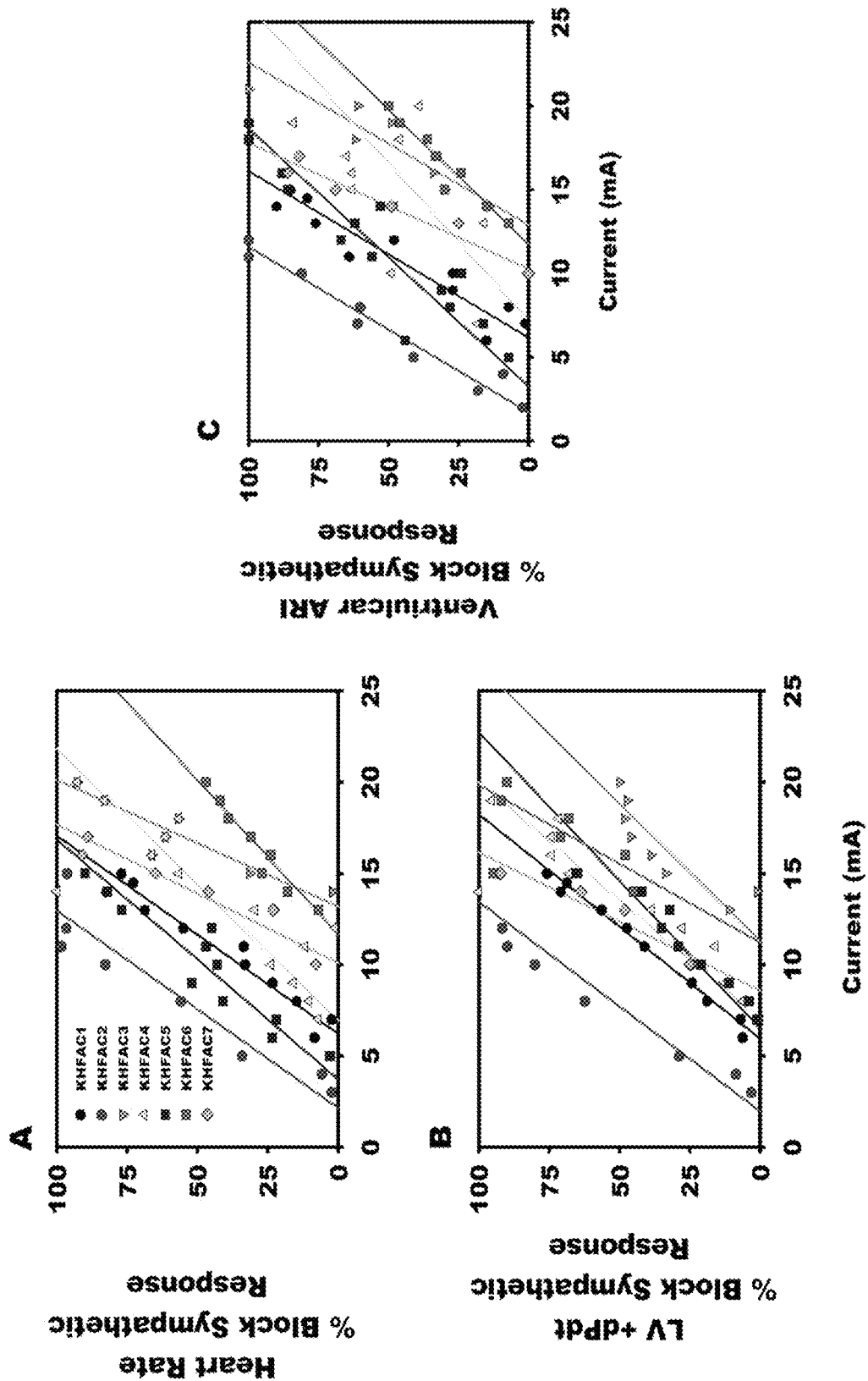
FIG. 5A-FIG. 5C, depicts results demonstrating that KHFAC block is scalable: the degree of inhibition of cardiac responses to right sympathetic stimulation (% block sympathetic response) at fixed KHFAC frequency and with randomized stimulus intensities is shown. Note that the sympathetic-evoked changes in heart rate (FIG. 5A), left ventricular +dP/dt (FIG. 5B), and ventricular activation recovery intervals (ARI.

It was also observed that KHFAC block is scalable (FIG. 5A-FIG. 5C). For example, FIG. 5A-FIG. 5C shows the percentage block of the sympathetic efferent-evoked cardiac responses to right sympathetic stimulation (% block sympathetic response) at fixed KHFAC frequency and with randomized stimulus intensities. Note that the sympathetic-evoked changes in heart rate (FIG. 5A), left ventricular +dP/dt (FIG. 5B), and ventricular activation recovery intervals (ARI; FIG. 5C) were progressively decreased with increases in stimulus intensity. 0% reflects no block (full sympathetic response) and 100% reflects complete functional block of sympathetic efferent projections to the heart.

It was also observed that KHFAC block demonstrates persistence and memory. FIG. 6A-FIG. 6C depicts the effects of 20 minutes KHFAC on the percentage block of the sympathetic evoked responses during and after KHFAC. Sympathetic stimulation from right T1 (if KHFAC deployed to ansae) or right T2 (if KHFAC deployed between T1-T2 paravertebral ganglia) was performed at 1 minute, 10 minutes, and 20 minutes of KHFAC. Post KHFAC sympathetic stimulations were performed at 5 minutes and subsequently every 10 minutes for up to 1 hour or until recovery of the response. Shown are the hemodynamic responses for heart rate (FIG. 6A), LV +dP/dt (FIG. 6B) and Ventricular ARI (FIG. 6C). In some cases there was a rebound of the sympathetic response after the 20 minutes of KHFAC with augmented responses (% Rebound). In one animal (KHFAC2) the hemodynamic indices did not recover. In this case, stimulation through the KHFAC electrode (4 hz, 4 ms) demonstrated a normal sympathetic response indicating nerve viability.

The time course of KHFAC onset is shown in FIG. 7A-FIG. 7D. FIG. 7A and FIG. 7B shows the time to peak for the various onset responses at initiation of KHFAC for heart rate and LV +dp/dt respectively. Note that the time to peak onset is relatively constant across the all stimulus protocols (frequency and intensity). FIG. 7C shows the time from start of onset to 66% recovery to baseline for heart rate for all stimulus protocols. Overall, the duration of the onset response is directly related to the magnitude of that response (FIG. 7C and FIG. 7D). Further, it is shown that the magnitude of onset does not directly relate to efficacy of block (FIG. 8).

The experiments presented herein demonstrate that with appropriate interface and KHFAC stimulation protocols, it is possible to achieve effective and high level block of sympathetic projections to heart with minimal onset response. It is shown herein that: KHFAC for sympathetic control of the heart is scalable and sustainable; KHFAC can be delivered to T1-T2 paravertebral chain or ansae subclavia with equivalent efficacy; and KHFAC can be effective in preemptive and reactive modes to mitigate sympatho-excitation. Further, it is demonstrated that there is memory to KHFAC, with return to normal sympathetic control within 5-10 min. In certain cases, there is a rebound post-KHFAC with some augmentations in chronotropic and dromotropic function. For onset response, time to peak is similar but with duration related to magnitude. The relationship of magnitude of onset response to magnitude of block is highly variable.

Example 2: VNS and Plasticity and Memory

Experiments were conducted to examine the effects of chronic VNS on changes in the plasticity and memory of the autonomic nervous system. FIG. 9A-FIG. 9B depicts the results of experiments demonstrating that in adult canines, bilateral non-restrictive renal wrap (RW) induces chronic hypertension. The representative changes in cardiac structure with chronic RW and effects of cervical VNS system implanted at day 99 and activated on day 102 is shown in FIG. 10. Note the reverse remodeling in cardiac hypertrophy in association with VNS onset indicating both memory and plasticity in the system.

FIG. 11A-FIG. 11D demonstrates that RW is a model of preserved ejection heart failure (HFpEF). Reactive cervical VNS reverse remodels in part the induced hypertrophy.

It is shown that VNS applied to right cervical vagus (RCV) preserves sympathetic function and reverse remodels parasympathetic control towards normal levels; likewise reducing pulmonary wedge pressure while preserving cardiac output (FIG. 12A-FIG. 12D). Further, VNS applied to right cervical vagus (RCV) does not reverse remodel parasympathetic control exerted from the contralateral vagus (FIG. 13). The data for various cardiac parameters obtained in control, RW, and RW+RCV groups is shown in the table of FIG. 14.

Example 3: SCS and Plasticity and Memory

Experiments were conducted to examine the effects of high thoracic spinal cord stimulation on changes in the plasticity and memory of the autonomic nervous system, its control of regional cardiac function and the impact on central neural elements of the cardiac nervous system. FIG. 15 demonstrates the increases in chamber volume, hyperdynamic cardiac responses as reflected in heart rate and left ventricular ejection fraction, and the abnormal pressure gradients between ventricle to atrium in response to mitral regurgitation. FIG. 16 demonstrates that reactive spinal cord stimulation imparts a survival benefit in animals with chronic myocardial infarction and mitral regurgitation. Chronic high thoracic SCS does not reverse remodel parasympathetic control of regional cardiac function (FIG. 17). However, high thoracic SCS partially restores basal cardiac function towards normal (FIG. 18) and reverse remodels/preserves functional sympathetic control of regional cardiac function (FIG. 19). The HF-induced increase in biochemical indices of sympathetic activation are normalized by SCS, as shown in FIG. 20.

Experiments were also conducted investigating cell loss and damage in the hippocampus. Coronal section of the Nissl stained frozen hippocampus is shown in FIG. 21A-FIG. 21C. Shown are representative coronal sections of post-fixed, paraffin-embedded, and Nissl-stained canine hippocampus from the three treatment groups of dogs (FIG. 21A, 4× view of whole hippocampus; FIG. 21B, 20× view of granular layer of the dentate gyrus; FIG. 21C, 40× view of CA3 neurons). Dentate gyrus neuronal densities estimated by measuring fractional areas occupied by neurons in the dentate gyrus are shown in FIG. 21D. Lines over bars show p values of designated group comparisons.

Experiments were also conducted to examine relative gene expression. Relative gene expression of caspase-3 (FIG. 22A), HIF-1α (FIG. 22B) and Glut-1 (FIG. 22C) in the hippocampus was measured from sham operated control (SHAM; n=8-9), chronic mitral regurgitation/myocardial infarction (MI/MR; n=8) and chronic MI/MR treated with spinal cord stimulation (MI/MR+SCS; n=6): Shown are the means±SEM of fold changes computed comparing treatment groups to the SHAM group. Only group comparisons of caspase-3 expression levels demonstrated statistical significance; lines over bars show p values of group comparisons for this gene.

FIG. 23 depicts the primer sequences used. The raw data for various cardiac parameters during the studies is shown in the table in FIG. 24. FIG. 25 summarizes the vascular biomarkers indicative of cardiac stress/damage in response to MI and then to MR induction 2 weeks later, and at termination. Blood sample obtained immediately prior to MI induction (baseline), at 2 and 14 days after MI induction, and at 2 day and 16 weeks post MR induction. *p≤0.05 from baseline; +p≤0.05 from 2 day post-MI; #p≤0.05 from 14 day post-MI (and just prior to MR induction).

FIG. 26 summarizes general definitions for neural network plasticity and neural network memory as specifically related to embodiments of this invention. It should be apparent to those skilled in the art that other embodiments and variations of this invention can be devised where delivery of energy from an external source can alter endogenous neural network structure or function to reverse adverse changes in autonomic control of evolving from pathophysiological conditions. It should also be apparent to those to those skilled in the art that other embodiments and variations of this invention can be devised where delivery of energy from an external source can impact endogenous neural network structure or function to counteract inherent abnormalities in autonomic control of that predispose to the development of pathophysiological conditions The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A system for modulating the plasticity and/or memory of the autonomic nervous system comprising one or more components for delivering energy to a nerve or ganglion of the autonomic nervous system, wherein the one or more components comprise one or more stimulating electrodes for applying an electrical stimulus, and wherein the stimulating electrodes are placed dorsal to and utilized in conjunction with one or more components for producing scalable block of efferent projecting axons to the heart.

2. The system of claim 1 further comprising one or more recording electrodes for measuring the activity of a nerve, activity of a ganglia, activity of a neuron, electrical activity of the heart, or biomarker levels within the heart or vasculature.

3. The system of claim 1, where the one or more components for producing scalable block of efferent projecting axons to the heart are configured for delivering energy for producing the scalable block, wherein the energy is selected from the group consisting of electrical energy, electromagnetic energy, acoustic energy, and thermal energy.

4. The system of claim 1, where block efficacy is evaluated in manual fashion or in close looped fashion and evoked changes in neural signals or cardiac signals are the sensory detect signal against which block efficacy is assessed.

5. A method for altering the function or plasticity of a neural structure comprising delivering, via the system of claim 1, energy to an autonomic neural structure comprising a nerve or ganglion of the autonomic nervous system, wherein the delivery of energy alters the function or plasticity of the neural structure during and beyond the delivery.

6. The method of claim 5, wherein the effects extend beyond the neural structure to which energy is delivered, to the greater autonomic network.

7. The method of claim 5, wherein energy is selected from the group consisting of electrical energy, electromagnetic energy, acoustic energy, and thermal energy.

8. The method of claim 5, wherein one or more electrodes are placed directly in or adjacent to the neural structure by direct surgical access or by vascular access.

9. The method of claim 5, wherein the neural structure is at least one selected from the group consisting of: a nerve or ganglia of an intrinsic cardiac nervous system, a nerve or ganglia of an intrathoracic nerve trunk, a nerve or ganglia of an cervical vagosympathetic nerve trunk, a nodose ganglia, a petrosal ganglia, a paravertebral sympathetic chain ganglia, a dorsal root ganglia, a spinal cord, and a peripheral distribution of a $9^{th}$, $10^{th}$, or $12^{th}$ cranial nerve.

10. The method of claim 5, wherein the method alters a neural network structure, and wherein the alteration includes one or more changes selected from the group consisting of changes in: neuronal apoptosis potential, neural network interconnectivity, neuronal phenotype, receptors and the neural-myocyte interface.

11. The method of claim 5, wherein, the method comprises directly altering the neural structure to which energy is delivered.

12. The method of claim 5, wherein the method comprises altering a neural structure that is rostral and/or caudal to the neural structure to which energy is delivered.

13. The method of claim 5, wherein the energy is delivered acutely or chronically.

14. The method of claim 5, wherein neuronal function is altered in a subset or subsets of neurons contained within intrathoracic ganglia including afferents, local circuit, sympathetic or parasympathetic soma.

15. The method of claim 5, wherein neuronal function is altered in primary cardiovascular afferent associated with a dorsal root, petrosal or nodose ganglia and their projections to brainstem and spinal cord neural networks.

16. The method of claim 5, wherein the delivery of energy is delivered in an open loop by an external control, or is delivered in a closed-loop.

17. The method of claim 16, wherein the energy is delivered upon the detection of a signal.

18. The method of claim 17, wherein the signal comprises the identification of neural signature or recordings indicative of adverse autonomic activity and that is recorded from electrodes placed into or on intrathoracic ganglia, intrathoracic axonal projections, cervical vagosympathetic nerve trunk, or paravertebral ganglia.

19. The method of claim 17, wherein the signal comprises the identification of neural signature or recordings indicative of adverse cardiovascular activity and that is recorded from electrodes placed into or on nodose, petrosal or dorsal root ganglia.

20. The method of claim 17, wherein the signal comprises detection of one or more abnormal chemicals or biomarkers, as detected from one or more sensors within the heart muscle, cardiac chambers or other intravascular sites.

* * * * *